(12) United States Patent
Stokes et al.

(10) Patent No.: US 10,557,810 B2
(45) Date of Patent: Feb. 11, 2020

(54) ICE NUCLEATING PARTICLE SPECTROMETER

(71) Applicant: THE REGENTS OF THE UNIVERSITY OF CALIFORNIA, Oakland, CA (US)

(72) Inventors: Malcolm Stokes, La Jolla, CA (US); Charlotte M. Beall, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 202 days.

(21) Appl. No.: 15/724,079

(22) Filed: Oct. 3, 2017

(65) Prior Publication Data
US 2018/0100818 A1    Apr. 12, 2018

Related U.S. Application Data

(60) Provisional application No. 62/405,096, filed on Oct. 6, 2016.

(51) Int. Cl.
| | |
|---|---|
| *G01N 25/06* | (2006.01) |
| *G01J 3/28* | (2006.01) |
| *F25B 9/00* | (2006.01) |
| *G01W 1/00* | (2006.01) |
| *G08B 21/18* | (2006.01) |
| *G08B 19/02* | (2006.01) |

(52) U.S. Cl.
CPC .............. *G01N 25/06* (2013.01); *F25B 9/006* (2013.01); *G01J 3/2823* (2013.01); *G01W 1/00* (2013.01); *G08B 21/187* (2013.01); *G08B 19/02* (2013.01)

(58) Field of Classification Search
CPC ...... G01J 3/2823; G01J 1/20; G01J 2003/003; G01N 2021/1731; G01N 23/20033; F25D 31/003
See application file for complete search history.

(56) References Cited

U.S. PATENT DOCUMENTS

| | | | |
|---|---|---|---|
| RE32,933 E * | 5/1989 | Vander Schaaf ....... | F25D 17/06 165/61 |
| 5,469,712 A * | 11/1995 | Sitte ........................ | F17C 3/085 62/51.1 |
| 6,170,267 B1 * | 1/2001 | Kitaoka .................... | B01L 7/00 62/3.6 |
| 2002/0148239 A1 * | 10/2002 | Trieskey ................... | F25B 5/02 62/79 |
| 2006/0274151 A1 * | 12/2006 | Lueerssen ............. | G01J 5/0003 348/180 |

(Continued)

OTHER PUBLICATIONS

Baustian et al., "Depositional ice nucleation on solid ammonium sulfate and glutaric acid particles", Atmos. Chem. Phys. Discuss. 9, 20949-20977, doi:10.5194/acp-10-2307-2010, 2010.

(Continued)

*Primary Examiner* — Cassey D Bauer
(74) *Attorney, Agent, or Firm* — Perkins Coie LLP

(57) ABSTRACT

Methods, systems, and devices are disclosed for implementing an exemplary immersion mode ice spectrometer. In order to increase sample throughput and improve accuracy of Ice Nucleating Particle (INP) freezing temperature measurement, the exemplary immersion mode ice spectrometer both increases sample cooling rates and monitors changes in optical properties of water droplets during freezing.

16 Claims, 17 Drawing Sheets

(56) References Cited

U.S. PATENT DOCUMENTS

| | | | | |
|---|---|---|---|---|
| 2008/0029248 | A1* | 2/2008 | Magnant | B01L 7/00 165/104.19 |
| 2012/0285872 | A1* | 11/2012 | Shreve | F25B 21/02 210/149 |
| 2012/0304671 | A1* | 12/2012 | Hallett | F25C 1/00 62/66 |
| 2013/0301781 | A1* | 11/2013 | Parvin | G21C 15/18 376/282 |
| 2014/0202179 | A1* | 7/2014 | Batey | F25D 29/001 62/62 |
| 2014/0354868 | A1* | 12/2014 | Desmarais | H04N 5/23293 348/333.01 |
| 2015/0355061 | A1* | 12/2015 | Inoue | G01N 1/42 73/863.11 |
| 2018/0024032 | A1* | 1/2018 | Hollabaugh | G01N 1/42 475/331 |
| 2018/0067039 | A1* | 3/2018 | Johnston | G01N 17/002 |
| 2018/0136118 | A1* | 5/2018 | Kueny | G01N 21/73 |
| 2019/0120753 | A1* | 4/2019 | Prater | G01N 21/35 |
| 2019/0283029 | A1* | 9/2019 | German | F25D 25/00 |
| 2019/0293344 | A1* | 9/2019 | Sun | A01N 1/0257 |

OTHER PUBLICATIONS

Beall et al., "Automation and heat transfer characterization of immersion mode spectroscopy for anlysis of ice nucleating particles", Atmos. Meas. Tec., 10, 2017, pp. 2613-2626.
Benchikn et al., "Photothermal measurement of the thermal conductivity of supercooled water", Sci. York, 46, 727-731, 1985.
Biddle et al., "Thermal conductivity of supercooled water", Phys. Rev. E—Stat. Nonlinear, Soft Matter Phys., 87, 1-7, doi: 10.1103/PhysRevE.87.04230, 2013.
Brunauer et al., "Adsorption of Gases in Multimolecular Layers", J. Am. Chem. Soc. 60, 309-319, doi: 10.1021/ia01269a023, 1938.
Budke et al., "BINARY: An optical freezing array for assessing temperature and time dependence of heterogeneous ice nucleation", Atmos. Meas. Tech., 8(2), 689-703, doi:10.5194/amt-8-689-2015, 2015.
Burrows et al., "Ice nuclei in marine air: biogenic particles or dust?", Atmos. Chem. Phys., 13(1), 245-267, doi:10.5194/acp-13-245-2013, 2013.
Creamean et al., "Dust and biological aerosols from the Sahara and Asia influence precipitation in the western U.S.", Science, 339(6127), 1572-8, doi:10.1126/science.1227279, 2013.
Cziczo et al., "Clarifying the Dominant Sources and Mechanisms of Cirrus Cloud Formation", Science, (May), 1-8, doi:10.1126/science.1234145, 2013.
Dehaoui et al., "Viscosity of deeply supercooled water and its coupling to molecular diffusion", Proc. Natl. Acad. Sci., 112(39), 12020-12025, doi:10.1073/pnas.1508996112, 2015.
DeMott et al., Measurements of the concentration and composition of nuclei for cirrus formation:, Proc. Natl. Acad. Sci. U. S. A., 100(25), 14655-60, doi:10.1073/pnas.2532677100, 2003.
DeMott et al., "Predicting global atmospheric ice nuclei distributions and their impacts on climate", Proc. Natl. Acad. Sci. U. S. A., 107(25), 11217-22, doi:10.1073/pnas.0910818107, 2010.
DeMott et al., "Sea spray aerosol as a unique source of ice nucleating particles", Proc. Natl. Acad. Sci., 113(21), 201514034, doi:10.1073/pnas.1514034112, 2015.

Hill et al., "Measurement of ice nucleation-active bacteria on plants and in precipitation by quantitative PCR", Appl. Environ. Microbiol. 80, 1256-1267, doi:10.1128/AEM.02967-13, 2014.
Hiranuma et al., "A comprehensive laboratory study on the immersion freezing behavior of illite NX particles: a comparison of seventeen ice nucleation measurement techniques", Atmos. Chem. Phys. Discuss., 14, accepted, doi:10.5194/acpd-14-22045-2014, 2014a.
Hiranuma et al., "Influence of surface morphology on the immersion mode ice nucleation efficiency of hematite particles", Atmos. Chem. Phys., 14(5), 2315-2324, doi:10.5194/acp-14/2315-2014, 2014b.
Hoose et al., "A Classical-Theory-Based Parameterization of Heterogeneous Ice Nucleation by Mineral Dust, Soot, and Biological Particles in a Global Climate Model", J. Atmos. Sci., 67(8), 2483-2503, doi:10.1175/2010JAS3425.1, 2010.
Kell et al., "Density, Thermal Expansivity, and Compressibility of Liquid Water from 0" to 150° C.: Correlations and Tables for Atmospheric Pressure and Saturation Reviewed and Expressed on 1968 Temperature Scale", J. Chem. Eng. Data, 20(1), 97-105, doi:10.1021/je60064a005, 1975.
Klein et al., "A new method for sampling of atmospheric ice nuclei with subsequent analysis in a static diffusion chamber", Atmos. Res., 96(2-3), 218-224, doi:10.1016/j.atmosres.2009.08.002, 2010.
Phillips et al., "Simulations of the glaciation of a frontal mixed-phase cloud with the Explicit Microphysics Model", Q. J. R. Meteorol. Soc., 129(590), 1351-1371, doi:10.1256/qj.02.100, 2003.
Rogers et al., "Measurements of ice nucleating aerosols during SUCCESS". Geophys Res Lett 25:1383-1386, doi:10.1029/97GL03779, 1998.
Seinfeld et al., "Improving our fundamental understanding of the role of aerosol-cloud interactions in the climate system", Proc. Natl. Acad. Sci., 113(21), 5781-5790, doi:10.1073/pnas.1514043113, 2016.
Stopelli et al., "Freezing nucleation apparatus puts new slant on study of biological ice nucleators in precipitation", Atmos. Meas. Tech., 7(1), 129-134, doi:10.5194/amt-7-129-2014, 2014.
Stopelli et al., "Predicting abundance and variability of ice nucleating particles in precipitation at the high-altitude observatory Jungfraujoch", (February), 1-18, doi:10.5194/acp-2016-108, 2016.
Tobo, "An improved approach for measuring immersion freezing in large droplets over a wide temperature range", Sci. Rep., Apr. 6, 32930, doi:10.1038/srep32930, 2016.
Trenberth et al., "Simulation of present-day and twenty-first-century energy budgets of the southern oceans", J. Clim., 23(2), 440-454, doi:10.1175/2009JCLI3152.1, 2010.
Vali, "Quantitative Evaluation of Experimental Results an the Heterogeneous Freezing Nucleation of Supercooled Liquids", J. Atmos. Sci., 28(3), 402-409, doi:10.1175/1520-0469(1971)028<0402:QEOERA>2.0.CO;2, 1971.
Whale et al., "A technique for quantifying heterogeneous ice nucleation in microlitre supercooled water droplets", Atmos. Meas. Tech., 8(6), 2437-2447, doi:10.5194/amt-8-2437-2015, 2015.
Wise et al., "Internally mixed sulfate and organic particles as potential ice nuclei in the tropical tropopause region", Proc. Natl. Acad. Sci. U. S. A., 107(15), 6693-8, doi:10.1073/pnas.0913018107, 2010.
Wright et al., "Minimal cooling rate dependence of ice nuclei activity in the immersion mode", J. Geophys. Res. Atmos., 118(18), 10535-10543, doi:10.1002/jgrd.50810, 2013.
Yousef et al., "Free Convection Heat Transfer From Upward-Facing Isothermal Horizontal Surfaces", J. Heat Transfer, 104(3), 493, doi:10.1115/1.3245120, 1982.

* cited by examiner

ICE NUCLEATING PARTICLE SPECTROMETER

PRIORITY CLAIM AND RELATED APPLICATION

This application claims the benefits and priority of U.S. Provisional Application No. 62/405,096 entitled "AUTOMATED ICE NUCLEATING PARTICLE SPECTROMETER" filed on Oct. 6, 2016, the entire disclosure of which is incorporate by reference as part of this application.

STATEMENT REGARDING FEDERALLY SPONSORED RESEARCH OR DEVELOPMENT

This invention was made with government support under grant no. CHE-1305427 awarded by the National Science Foundation (NSF). The government has certain rights in the invention.

TECHNICAL FIELD

This patent document relates to systems, devices, and processes to study the ice-nucleating properties of particles.

BACKGROUND

Ice nucleating particles (INPs) induce freezing of cloud droplets at temperatures above their homogeneous freezing-point (approximately −38° C.) and at a relative humidity (RH) below the homogeneous freezing RH of aqueous solution droplets at lower temperatures. Accordingly, INPs influence cold cloud lifetime, phase, and their optical and microphysical properties. INPs are comprised of a diverse population of particles, some species of which have complex sources and sinks.

Developing a parameterization of INPs in global climate models (GCMs) that result in a credible representation of global cloud coverage and the radiative balance remains a challenge. In situ observations to close critical knowledge gaps, such as the vertical distribution of INPs in the air column, the complex sources and sinks of biological INPs, and INP influence on cloud microphysics, are identified as a high priority for the improvement of INP representation in GCMs. One of the largest biases in shortwave reflectivity exists over the Southern Ocean, and this bias may be influenced by poor representation of INPs over primarily oceanic regions. Measurements of INP number distributions, particularly in remote ocean regions are needed to help develop parameterization of ice nucleation for use in cloud-resolving models and GCMs. To further improve the parameterization of INPs in GCMs, both field and laboratory measurements are needed to identify drivers of ice nucleation in clouds. Accurately defining the activation temperature of INPs assists in understanding the influence of INPs on clouds and improving representation of INPs in GCMs because INP freezing temperatures influence cloud phase and lifetime in mixed-phase clouds, or the supersaturation or temperature conditions in which ice clouds can form. An accuracy of the INP concentrations applied in cloud and climate models to within a factor of ten can avoid biases that lead to significant differences in cloud radiative and microphysical properties.

SUMMARY

Techniques, systems, and devices are disclosed for implementing an exemplary droplet assay technique known as immersion mode ice spectroscopy. In an exemplary embodiment, an ice spectrometer can increase the sample throughput and can improve accuracy of INP freezing temperature measurement by both increasing sample cooling rates and using camera to monitor changes in optical properties of water droplets during freezing.

An exemplary embodiment discloses a spectrometer. The exemplary spectrometer comprises a housing located on top of a chiller unit. The chiller unit comprises a cavity configured to be filled with a coolant, and a coil positioned to be submerged in presence of the coolant. The spectrometer also includes a hose to supply cold gas from the coil to a well area in the housing, the hose having a first end and the second end, wherein the first end is coupled to one end of the coil and the second end is coupled to a side of the housing, one or more metal blocks located inside the cavity of the chiller unit and positioned to be partially immersed in the coolant, wherein each metal block has a top surface with a plurality of indentations, a thermistor located in one of the one or more metal blocks to measure temperature of a region surrounding the one or more metal blocks, one or more sample trays located on top of the one or more metal blocks, wherein each sample tray comprises a plurality of wells that extend downwards from a bottom of each sample tray and that fit within the plurality of indentations of the one or more metal blocks, a lid to cover the plurality of wells to insulate air above the plurality of wells from room temperature air, a camera located on a top surface of the housing to capture images of samples located in the plurality of wells, a plurality of light sources located on the housing to provide a stable lighting environment in the housing, and a computing device comprising a processor and a memory including instructions stored thereon, wherein the instructions upon execution by the processor configure the computing device to: program the chiller unit to reach a certain end temperature to freeze samples located in the plurality of wells, and record, using the camera, an intensity of light reflected from the samples located in the plurality of wells at least during the temperature of the chiller unit is adjusted.

In some embodiments, the chiller unit is programmed by the computing device configured to send instruction indicative of an option for temperature control of the chiller unit; and selectively based on the option chose between a ramp function and a stepwise adjustment function.

In some embodiments, in response to the option being the ramp function, the computing device configured to: set a temperature of the chiller unit to reach the certain end temperature, read a current temperature of the chiller unit, adjust the temperature in response to a determination that the current temperature is greater than the certain end temperature, and wait for a certain amount of time in response to a determination that the current temperature is equal to the certain end temperature within a tolerance value.

In some embodiments, in response to the option being the stepwise adjustment function, the computing device configured to: set a temperature of the chiller unit to reach an intermediate temperature value, read a current temperature of the chiller unit, adjust the temperature in response to a determination that the current temperature is greater than the intermediate temperature value, wait a predetermined time interval in response to a determination that the current temperature is equal to the intermediate temperature value within a tolerance value, increase a predetermined variable, and set the temperature of the chiller unit to reach another intermediate temperature value.

In some embodiments, the intermediate temperature value is equal to a start temperature minus the predetermined variable multiplied by a temperature interval.

In some embodiments, the intensity of light is recorded by the computing device configured to: record, using the camera, a first mean intensity of light reflected from one or more samples in one or more wells at a first time value, record, using the camera, a second mean intensity of light reflected from the one or more samples in the one or more wells at a second time value, wherein the second time value logically comes after the first time value, and record a time, a freezing temperature measured using the thermistor, and a location of the one or more wells in response to a determination for each sample that an absolute value of a difference between the first mean intensity and the second mean intensity is greater than a predetermined threshold.

In some embodiments, the coil is a coiled copper tube. In some embodiments, the spectrometer further includes a splash guard fitted on the one or more metal blocks to prevent contamination of the plurality of wells by the coolant bath. In some embodiments, the one or more metal blocks comprise any one of aluminum, copper, and stainless steel.

In some embodiments, each of the one or more metal blocks includes a base with a cutout region. In some embodiments, the one or more sample trays comprises polypropylene. In some embodiments, the plurality of light sources are located on at least two sides of the housing.

In some embodiments, the lid includes Plexiglas material. In some embodiments, the housing is made from white cast acrylic sheet. In some embodiments, the spectrometer further includes an adjustable cradle that holds the camera and allows a camera lens to be aligned over a center region of the one or more metal blocks. In some embodiments, the thermistor is imbedded in the one or more metal blocks.

Another exemplary embodiment discloses a method for operating a spectrometer. The exemplary method comprises cooling nitrogen gas in a chiller unit, wherein the chiller unit including a coolant and a coil submerged in the coolant, and the coil is coupled to and receives dry nitrogen from an external supply, supplying the cooled nitrogen gas to a well region that includes one or more sample trays located on top of one or more blocks, wherein each sample tray comprises a plurality of wells, recording, using a camera, a first mean intensity of light reflected from one or more samples in one or more wells at a first time value, recording, using the camera, a second mean intensity of light reflected from the one or more samples in the one or more wells at a second time value, wherein the second time value logically comes after the first time value, and recording a time, a freezing temperature measured using a thermistor, and a location of the one or more wells by determining for each sample that an absolute value of a difference between the first mean intensity and the second mean intensity is greater than a predetermined threshold.

In some embodiments, the cooling of the nitrogen gas in the chiller unit comprises: sending instruction indicative of an option to control temperature of the chiller unit using a ramp function, setting the temperature of the chiller unit to reach the certain end temperature, reading a current temperature of the chiller unit, allowing the chiller unit to adjust the temperature in response to a determination that the current temperature is greater than the certain end temperature, waiting for a certain amount of time in response to a determination that the current temperature is equal to the certain end temperature within a tolerance value.

In some other embodiments, the cooling of the nitrogen gas in the chiller unit comprises: sending instruction indicative of an option to control temperature of the chiller unit using a stepwise adjustment function, setting the temperature of the chiller unit to reach an intermediate temperature value, reading a current temperature of the chiller unit, adjusting the temperature in response to a determination that the current temperature is greater than the intermediate temperature value, waiting a predetermined time interval in response to a determination that the current temperature is equal to the intermediate temperature value within a tolerance value, increasing a predetermined variable, and setting the temperature of the chiller unit to reach another intermediate temperature value.

In some embodiments, the intermediate temperature value is equal to a start temperature minus the predetermined variable multiplied by a temperature interval. In some embodiments, the coil is a coiled copper tube. In some embodiments, the one or more blocks comprise any one of aluminum, copper, and stainless steel. In some embodiments, each of the one or more metal blocks includes a base with a cutout region. In some embodiments, the one or more sample trays comprise polypropylene. In some embodiments, the thermistor is imbedded in the one or more blocks.

DETAILED DESCRIPTION

Figure 1A:
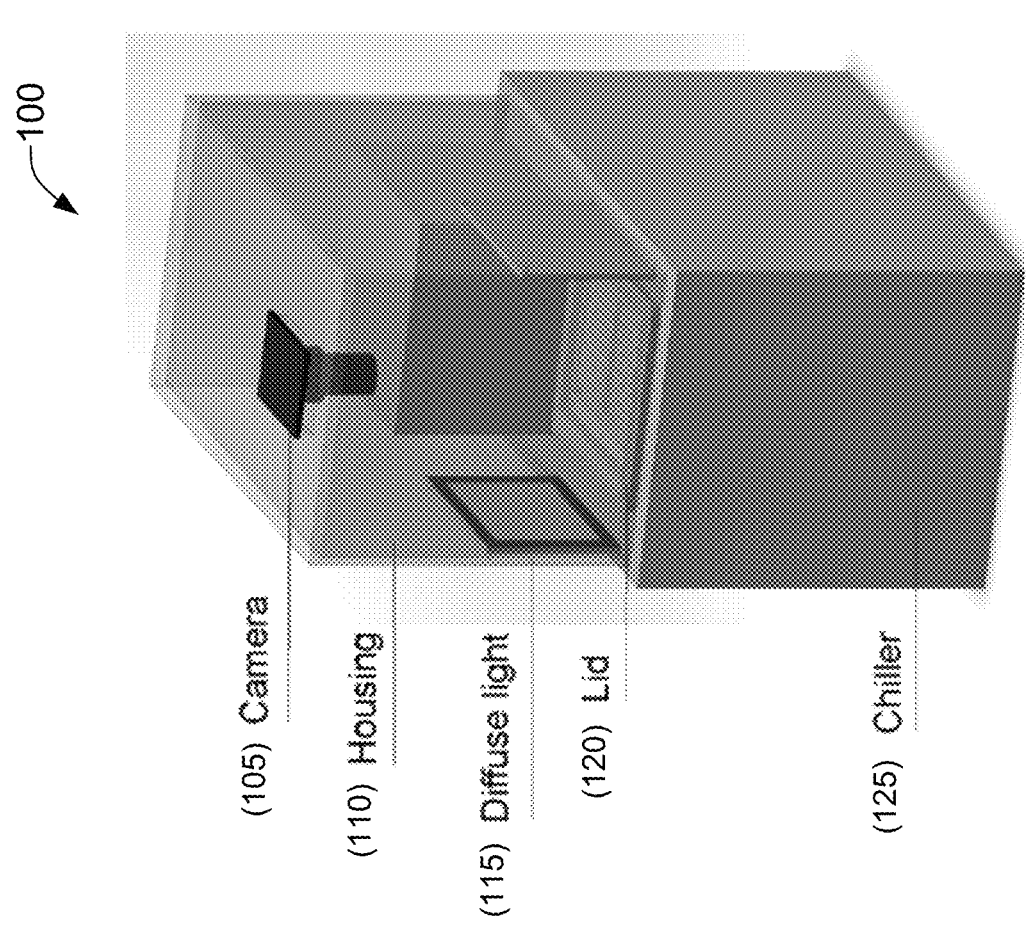
FIGS. 1A-1B shows an exemplary ice spectrometer.

Ice nucleating particles (INPs) influence cloud properties, such as phase or albedo, and can affect the overall precipitation efficiency. Developing a parameterization of INPs in global climate models has proven challenging. More INP measurements—including studies of their spatial distribution, sources and sinks, and fundamental freezing mechanisms—must be conducted in order to further improve INP parameterizations. In an exemplary embodiment, as further discussed below, an immersion mode INP measurement technique can determine optical changes of water droplets to detect freezing events. For the first time, heat transfer properties of the INP measurement technique are characterized using a finite-element-analysis-based heat transfer simulation to improve accuracy of INP freezing temperature measurement.

The heat transfer simulation is used to explain the sources of bias in temperature measurements in INP measurement techniques and ultimately explain the observed discrepancies in measured INP freezing temperatures between different instruments. The simulation results show that a difference of +8.4° C. between the well base temperature and the headspace gas results in an up to 0.6° C. stratification of the aliquot, whereas a difference of +4.2° C. or less results in a thermally homogenous water volume within the error of the thermal probe, ±0.2° C. The simulation results also show that there is a strong temperature gradient in the immediate vicinity of the aliquot, such that without careful placement of temperature probes, or characterization of heat transfer properties of the water and cooling environment, INP measurements can be biased toward colder temperatures. Based on a modified immersion mode technique, the exemplary ice spectrometer can be used to measure the standard test dust illite NX. The measurements from the exemplary ice spectrometer are compared against six other immersion mode droplet assay techniques that used wet suspensions. The exemplary ice spectrometer measurements of illite NX INP freezing temperatures compare reasonably with others, falling within the 5° C. spread in reported spectra. The exemplary ice spectrometer as well as its characterization of heat transfer properties allows higher confidence in accuracy of freezing temperature measurement, allows higher throughput of sample analysis, and enables disentanglement of the effects of heat transfer rates on sample volumes from time dependence of ice nucleation.

Several instruments and techniques exist, utilizing both online (real time) and offline (processed post-collection) approaches, for the measurement of INP number concentration and activation temperature across the range of ice nucleation mechanisms. Ice nucleation mechanisms include, for example, deposition nucleation, immersion, contact, and condensation freezing. However, some simulations find immersion freezing as the dominant ice nucleation mechanism globally from 1000 to 200 hPa; hence, most INP measurement techniques target immersion mode freezing. In Hiranuma et al. (2015), 17 online and offline immersion mode instruments were compared using illite NX as the dust standard. The major differences between the 17 instruments studied are described in detail therein; however in brief, the instruments fall into one of two categories: droplet assay techniques, in which INPs are immersed in water and distributed among an array of pico- to microliter scale droplets on a substrate and then cooled until frozen, or chamber techniques, in which droplets are passed through a temperature- and humidity-controlled chamber, where the freezing of droplets and their associated size change is detected with optical particle counters. Each of these techniques poses significant INP measurement challenges due to the rarity of INPs, which represent 1 in 106 or fewer of total aerosol particles, and mitigation requires large air sample volumes, which both limits the temporal sampling resolution and increases the chance of contamination, which can overwhelm subtle INP signals in the data. Making INP freezing temperature measurements can also present challenges, because sample droplets or crystals cannot be directly probed with thermal sensors throughout the cooling process without altering the fundamental shape or content of the droplet, and most thermal probes are not small enough to access nano- to microliter-sized droplets.

In an exemplary embodiment, an offline freezing assay technique for measurement of immersion mode INPs can determine optical changes of water volume arrays to detect freezing events. The offline freezing assay is an immersion mode technique that is similar to the immersion mode droplet assay, with one of the differences being in the type of substrate used. In both techniques, as further discussed in the sections below, multiple water volumes are supported on a substrate which is cooled until the water volumes are frozen, and concentrations of INPs as a function of freezing temperature are calculated from fractions of unfrozen droplets per temperature. In droplet assays, water volumes are distributed on a cold stage as droplets during measurements. However, in the freezing assay, as an example, small aliquots of water, typically around 50 μL each, are distributed in 1.2 mL wells within disposable polypropylene trays.

In an exemplary embodiment, as further discussed in the sections below, the trays can be mounted in metal blocks that are cooled during measurements. In some embodiments, the metal blocks can include any one of aluminum, copper, and stainless steel to facilitate thermal or heat conduction. One of the benefits of droplet or freezing assays is that it can provide an offline alternative for INP measurement with fewer aerosol size limitations than online chamber techniques. For regular sampling on any surface site, INP samples may be collected on open-face filters, which reduce sample inlet particle size biases and particle losses.

As further discussed below, the heat transfer properties of the exemplary INP Spectrometer instrument are characterized through a finite-element-analysis heat transfer simulation to evaluate the homogeneity of INP sample temperatures and identify optimal locations for the thermal probes. Finally, a standard test dust, such as illite NX, is tested using the instrument and is compared against the six other droplet array immersion mode INP measurement techniques that reported wet-suspension measurements of illite NX.

Theory of Operation of the Exemplary Spectrometer

Immersion mode ice spectroscopy measures INP concentrations at specific temperatures of a liquid sample. INP measurements of air samples can be made by collecting particles on a filter or via impinging particles into liquid, immersing the filter in ultrapure water, and shaking particles off of the filter by hand or via an automated rotator. The liquid sample is then distributed in microliter aliquots into a clean multiple well sample tray, such as a 96-well disposable polypropylene sample tray. An equal number and volume of aliquots of ultrapure water accompany each sample in the disposable tray as a control for contamination from the loading and/or ultrapure water. The sample trays are then inserted into a metal block that is cooled until the samples are frozen. The homogenous freezing point of water is −38° C., but either the 96-well sample tray surface or impurities present in the water induce freezing at higher temperatures, typically starting at −25 to −27° C., which limits the lower temperatures for which INP number concentrations may be assessed. Cumulative INP number concentrations per temperature per volume are calculated using the fraction of unfrozen wells f per given temperature interval:

$$INP = \frac{\ln(f)}{V} \qquad \text{Eq. (1)}$$

where V is the volume of the sample in each well. The fraction of unfrozen wells f is adjusted for contamination by subtracting the number of frozen ultrapure water wells per temperature interval from both the total number of unfrozen wells and the total number of wells of the sample.

Exemplary Design of the Ice Spectrometer

Figure 1B:
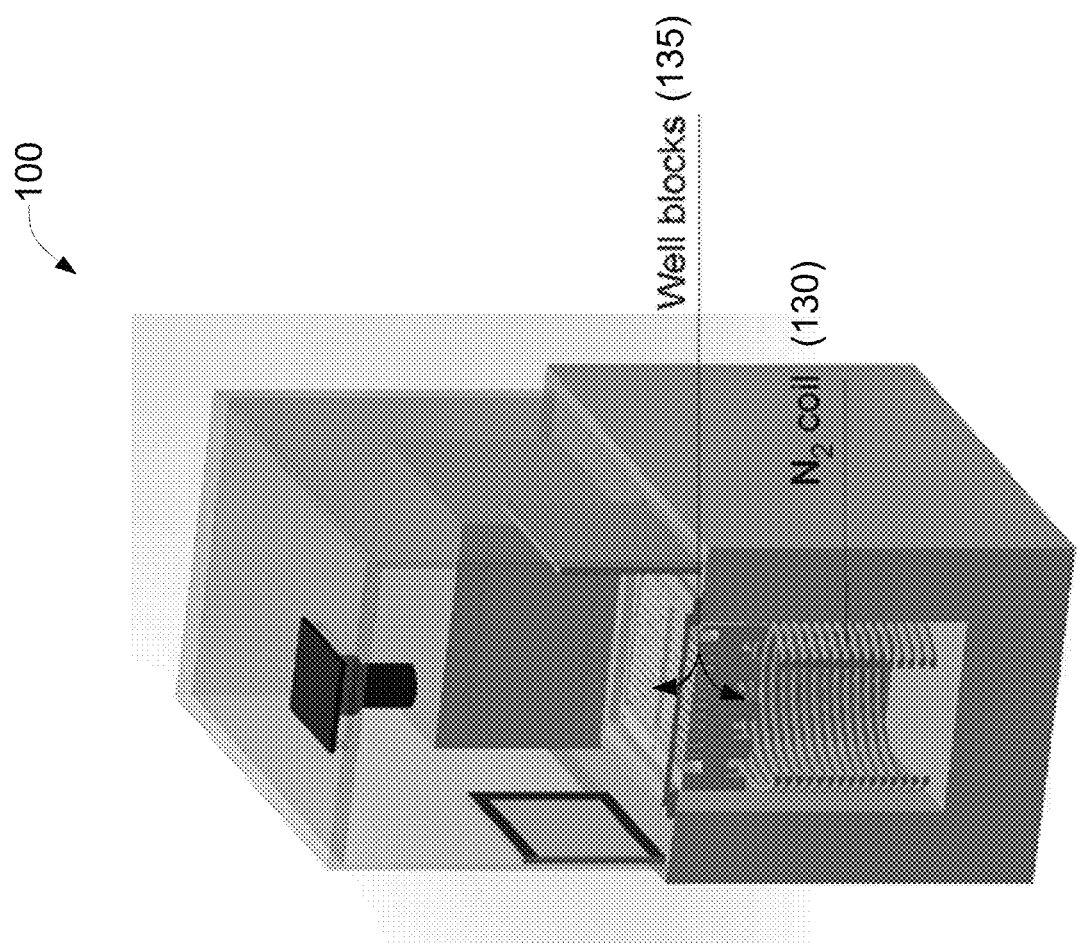

FIGS. 1A and 1B shows an exemplary ice spectrometer (100) that can increase sample throughput and improve accuracy of INP freezing temperature measurement. FIG. 1A shows an assembly of the various components of the exemplary ice spectrometer (100) that includes an insulated housing (110) placed on top of a chiller (125). FIG. 1B shows a cutout of an exemplary chiller (125). The ice spectrometer (100) is an immersion mode ice spectrometer that increase sample cooling rates and includes a software-controlled camera (105) that monitors changes in optical properties of water droplets during freezing. The exemplary ice spectrometer (100) has a maximum average cooling rate of $-0.87°$ C. $\min^{-1}$, as measured in the coolant bath in the chiller (not shown), from room temperature to $-33°$ C. that is used as an example for conducting measurements and simulations presented in this patent document. For the same temperature range, the average cooling rate as measured at the base of the well is the same. The role of cooling rate on freezing is not investigated at least because the role of cooling rate is known to influence freezing activation spectra to a much smaller extent than temperature alone.

FIG. 1B shows an exemplary ice spectrometer (100) that includes two metal well blocks (135) located or fixed inside the coolant bath (not shown) cavity of a chiller (125). The metal well blocks facilitate thermal or heat conduction. As mentioned above, the metal blocks can include aluminum, copper or stainless steel. In some embodiments, the chiller (125) can be a Fisher™ Isotemp™ refrigerated bath circulator. Each of metal block has a plurality of machined indentation cavities using which a disposable sample tray with a plurality of wells (not shown in FIGS. 1A-1B) is tightly fitted. In some embodiments, two sample trays can be used with each sample tray having 96-wells. Thus, in some embodiments, the top surface of each metal block can includes at least 96 indentation cavities to receive the 96-wells of each sample tray. In some embodiments, a single metal block can be used to receive a single sample tray. As discussed below, the sample tray including the plurality of wells may have a dark background, such as a black color, to assist in reflecting light recorded by the camera (105). A clear or transparent lid (120), such as a Plexiglas lid or acrylic plate caps a well region to insulate and isolate the air above the wells from room temperature air. As further discussed below, a clear or transparent lid allows the camera captures images of the samples in the wells to detect freezing events. The well region is generally the area in between the sample trays with the plurality of wells and the lid (120). The two metal well blocks (135) are fitted with a sealed splash guard (not shown) to prevent contamination of the well region by contact with the coolant.

Figure 2A:
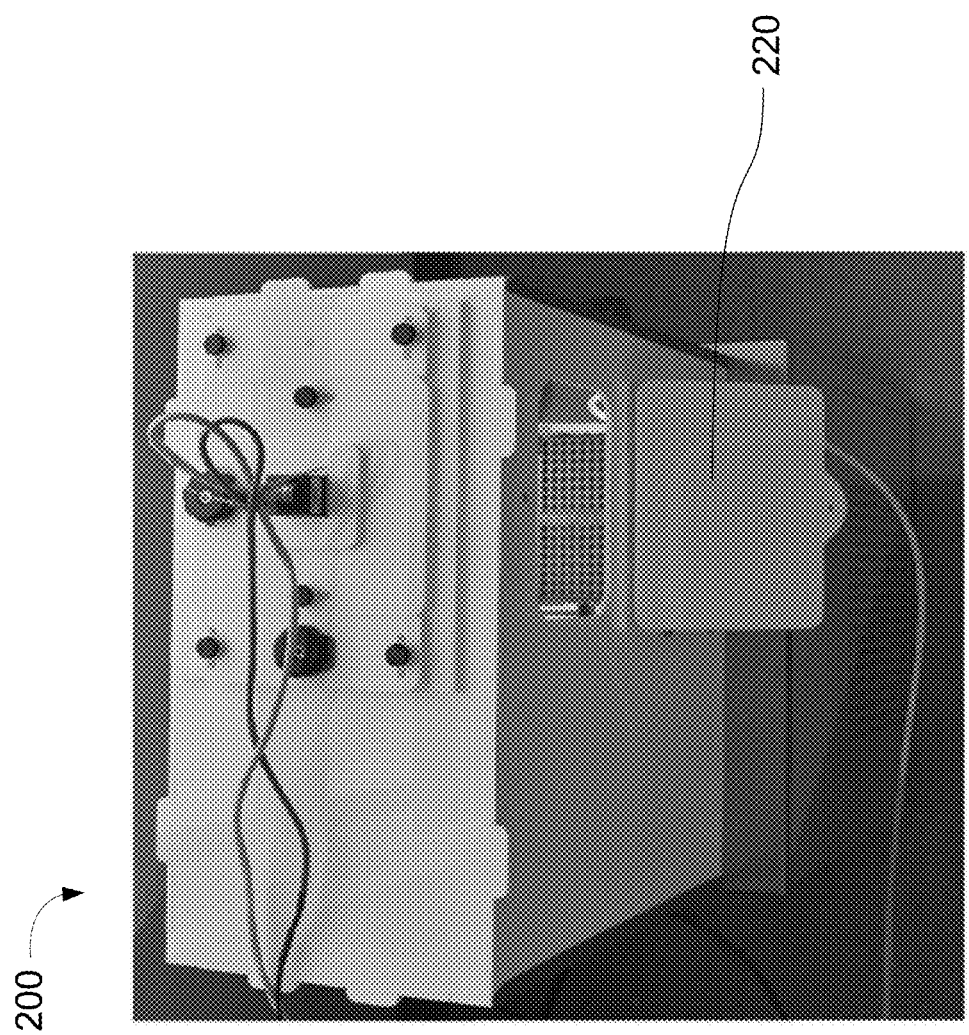
FIGS. 2A-2B show a top and side view of the exemplary ice spectrometer system.
Figure 2B:
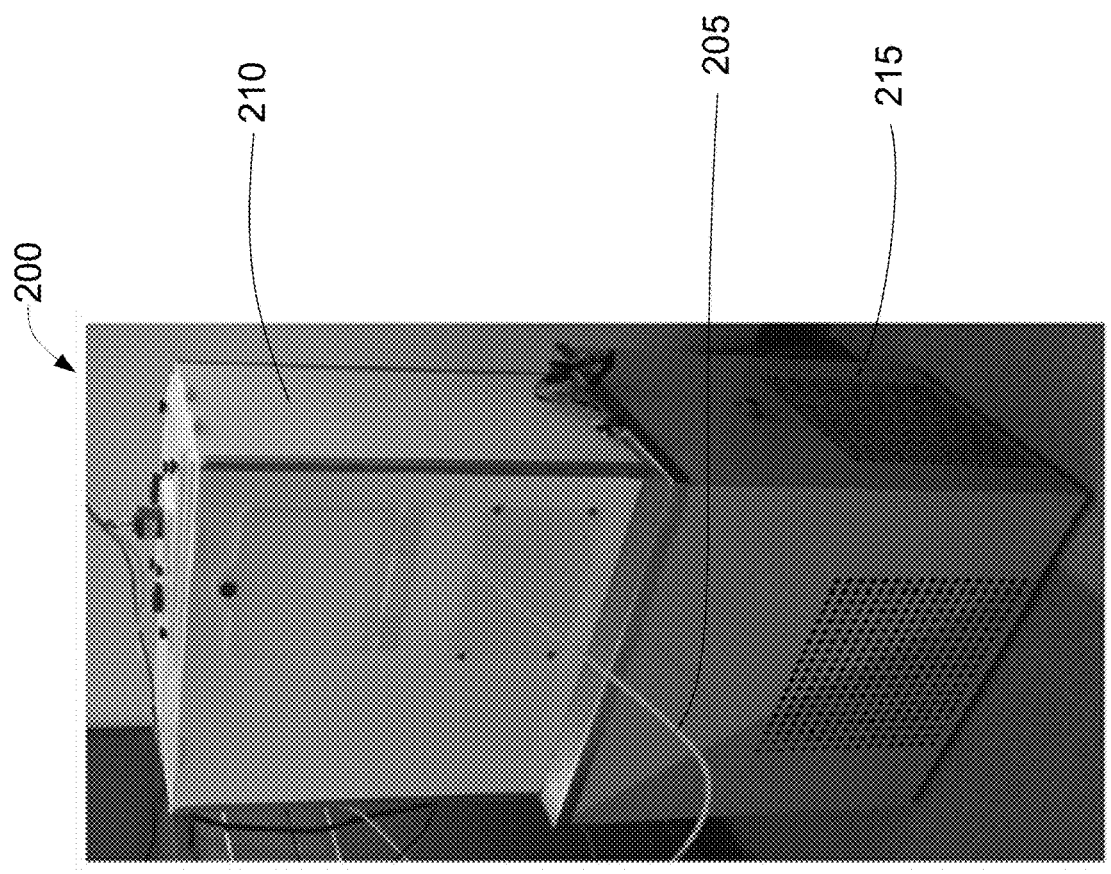

FIG. 2A shows a top-side view of the exemplary ice spectrometer (200). In FIG. 2A, the ice spectrometer (200) is shown with an open access door (220) that reveals the cooled well plate within the ice spectrometer. FIG. 2B shows an oblique view of the exemplary ice spectrometer (200) with the housing (210) located on top of the chiller unit (215). As discussed below, FIGS. 2A-2B show tubing (205) for the nitrogen gas supplied from the chiller (215) into the housing (210).

Figure 3:
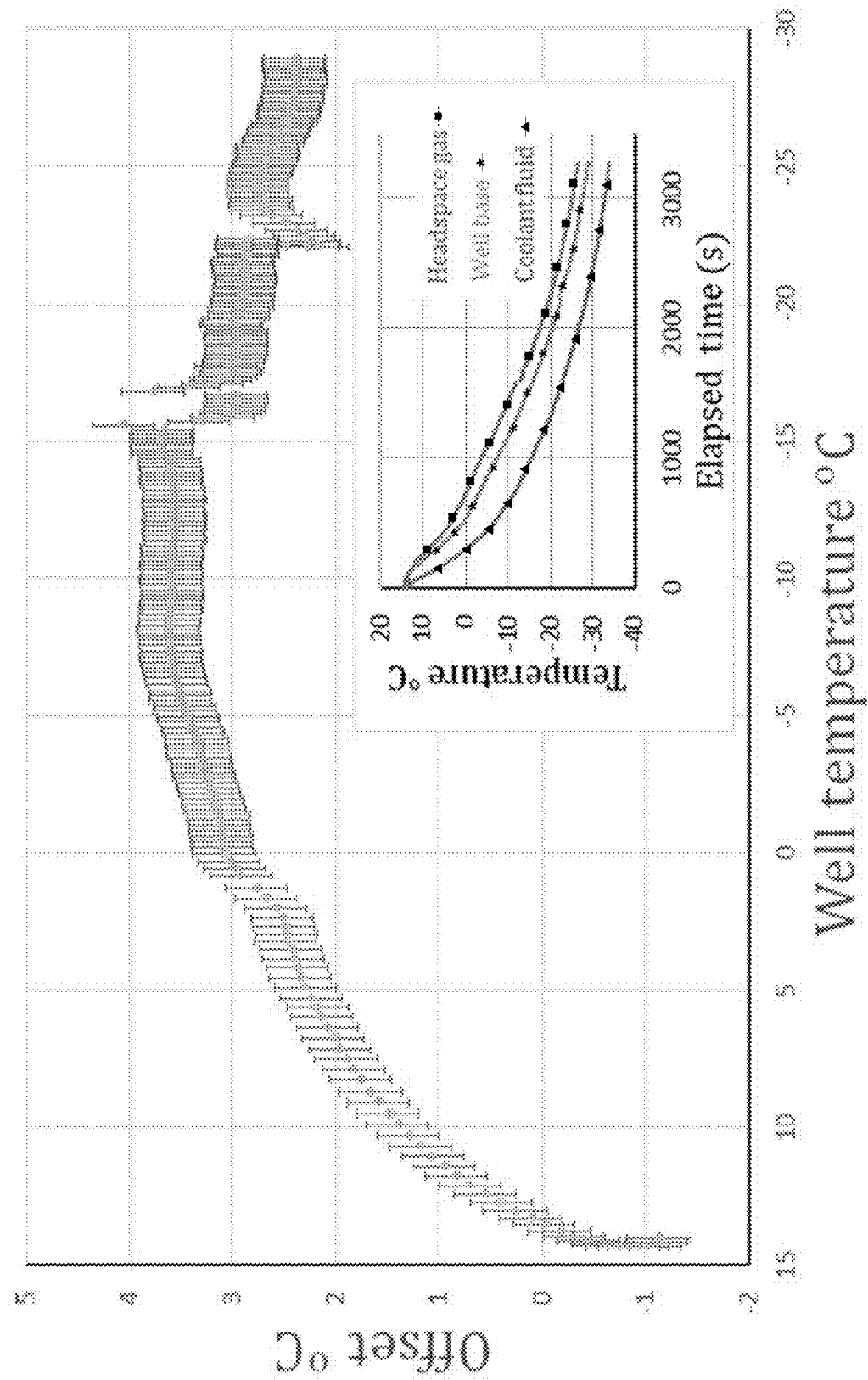
FIG. 3 shows a graph of well temperature vs. temperature offset measured between the base of the well and the air above the well as measured with a thermistor probe.

FIG. 1B also shows coiled tube (130) that is connected on one side to an external dry-nitrogen supply (not shown) and that lies or is submerged in the coolant bath beneath the metal well blocks (135) in order to cool nitrogen gas that is pumped through the other side of the coiled tube (130) into a hose or tube (not shown in FIG. 1B) that is coupled to a region of the housing (110) over the well region. FIG. 2B shows an exemplary ice spectrometer (200) with a tube (205) that is coupled on one side to the housing (110) over the well region and that is coupled on another side to the coiled tube (not shown in FIG. 2B) in the chiller (215). The tube (205) may be coupled to the housing (110) at a location that allows pre-chilled nitrogen gas to be provided to the well region or the space beneath the lid (120). In some embodiments, the coiled tube is a 1.8 mm long, 0.64 cm diameter copper tube. The cold nitrogen gas purges room temperature air away from the well region to decrease stratification of temperature within the sample volumes included in the plurality of wells of the sample tray. In some embodiments, the cool nitrogen gas is pumped over the well region at 0.25 L $\min^{-1}$. One reason for using a flow rate of 0.25 L $\min^{-1}$ is that it is found to most effectively cool the air above the well region. The nitrogen gas enters the well region significantly warmer than the chilled bath temperature (about $+11°$ C. as shown in the inset of FIG. 3) because the gas flows through approximately 15 cm of rubber tubing ((205) in FIG. 2B) exposed to the ambient room temperature before being injected beneath the transparent lid (120), and the headspace gas is not perfectly isolated from room air heat. In some embodiments, the tube (205) may have a shorter length to minimize exposure to ambient room temperature. At flow rates less than 0.25 L $\min^{-1}$, room temperature air leaks into the well region, but at significantly higher flow rates the fast-flowing nitrogen gas lifts the transparent lid ((120) in FIG. 1A), causing additional leakage.

Returning to FIG. 1A, a camera (105) is located on top of the housing (110). The camera (105) can monitor changes in optical properties of water droplets during freezing. In an exemplary embodiment, a 0.5-megapixel monochrome camera such as a Point Grey Blackfly 0.5 megapixel (MP) Mono GigE Power over Ethernet (POE) can be used to image the plurality of wells of the sample tray throughout the cooling process. As shown in FIG. 1A, the exemplary camera is fixed above the well region at the top of a plastic housing. The housing (110) can be fabricated from white cast acrylic sheet (e.g., 0.64 cm thick). An adjustable cradle holds the camera and allows aligning of the camera lens (e.g., 2.8-12 mm focal length, varifocal video lens, Edmund Optics) over a center region of the one or more metal blocks. Also fixed within each side of the white housing (110) are two backlights (115), e.g., white LED backlights from Edmund Optics, one backlight on either side of the well region. The backlights (115), which together provide a stable lighting environment for imaging of the wells and the liquid samples. After the camera (105) is aligned using the adjustable cradle, the video image can be live-streamed via the control software so that, for example, two 8×12 grids of 15×15 pixel squares are aligned over all 192 wells. In some embodiments, each 15×15 pixel box corresponds to an individual sample well, and the mean intensity of light reflected from each well is recorded. The 15×15 pixel dimension is just an example, and other pixel dimensions may be used by performing a trade-off between using too large a pixel area and missing freezing events because averaging tends to smoothen them out, and using too small a pixel area which makes the system susceptible to electronic and illumination noise, creating false positives. Furthermore, calculation of mean intensity is also provided as an example and other calculations and weighted averaging techniques may be used.

Figure 4A:
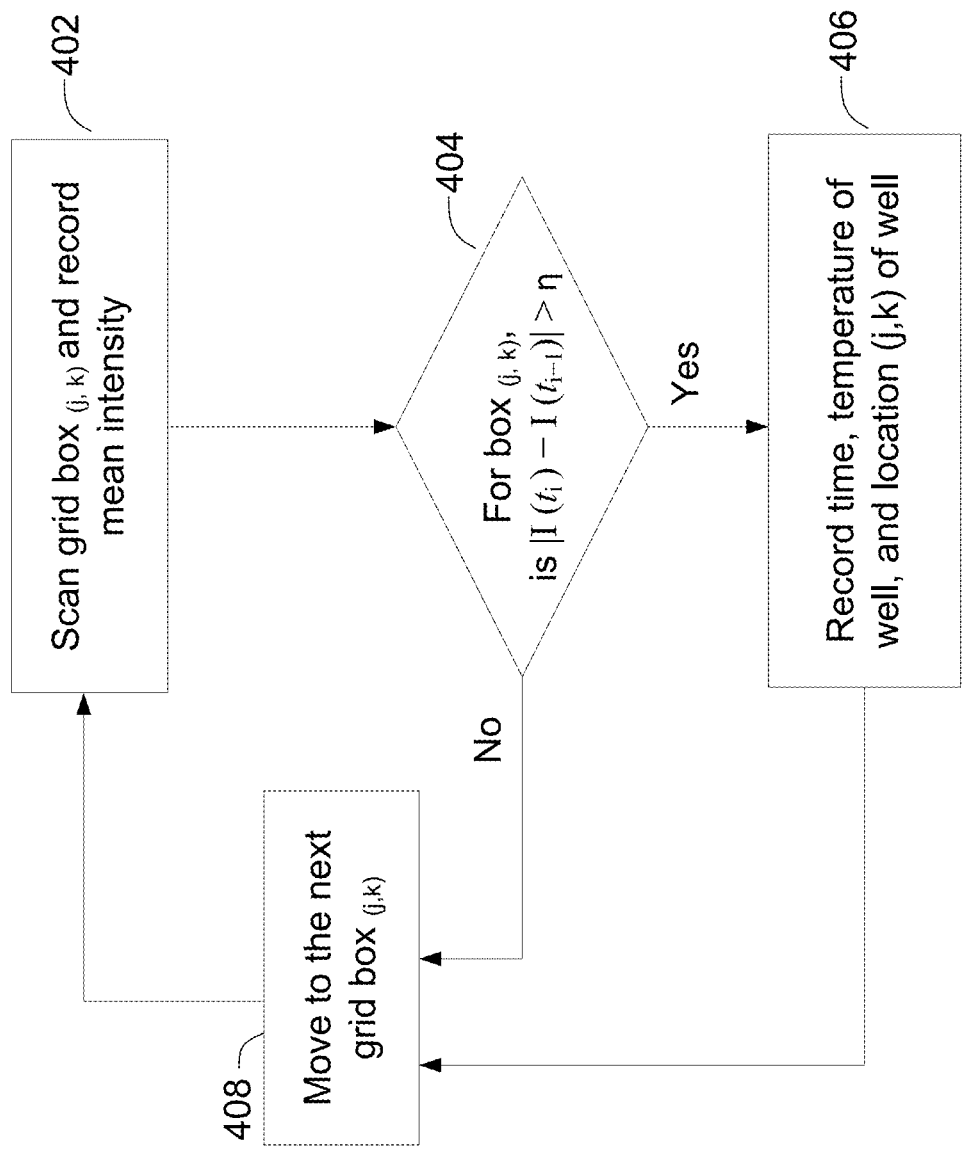
FIG. 4A shows an exemplary flow chart for regulating temperature of the exemplary ice spectrometer.
Figure 4B:
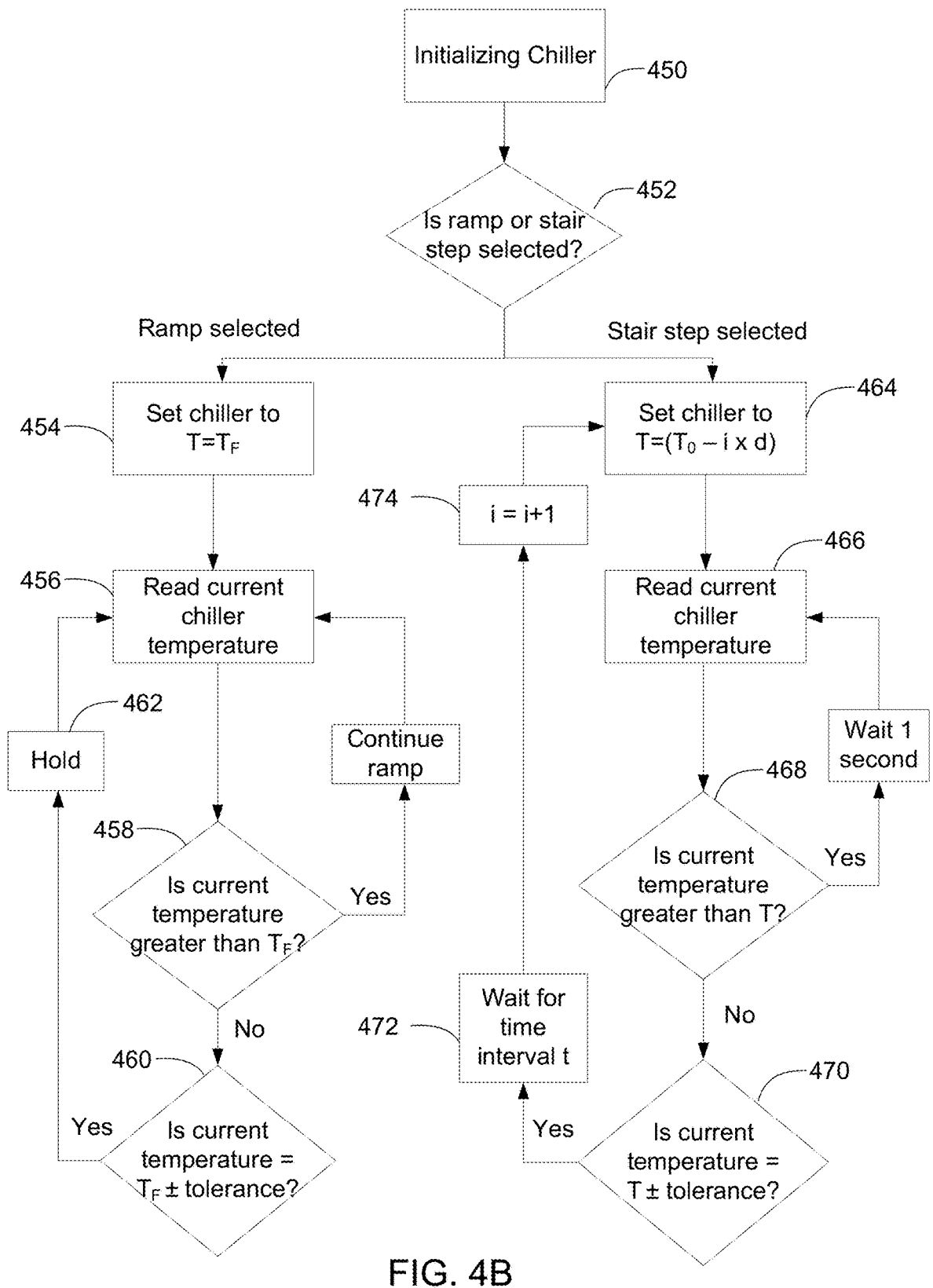
FIG. 4B shows an exemplary flow chart for detecting freezing events using camera and lights to leverage optical properties of phase change from water to ice.
Figure 4C:
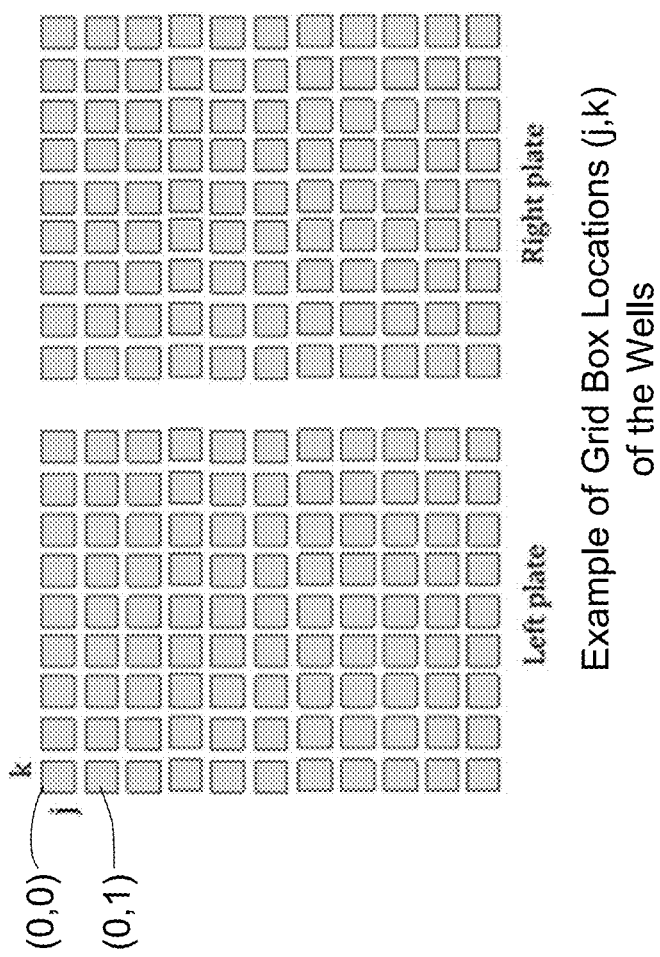
FIG. 4C shows an exemplary grid box locations of the wells of the sample tray.
Figure 5:
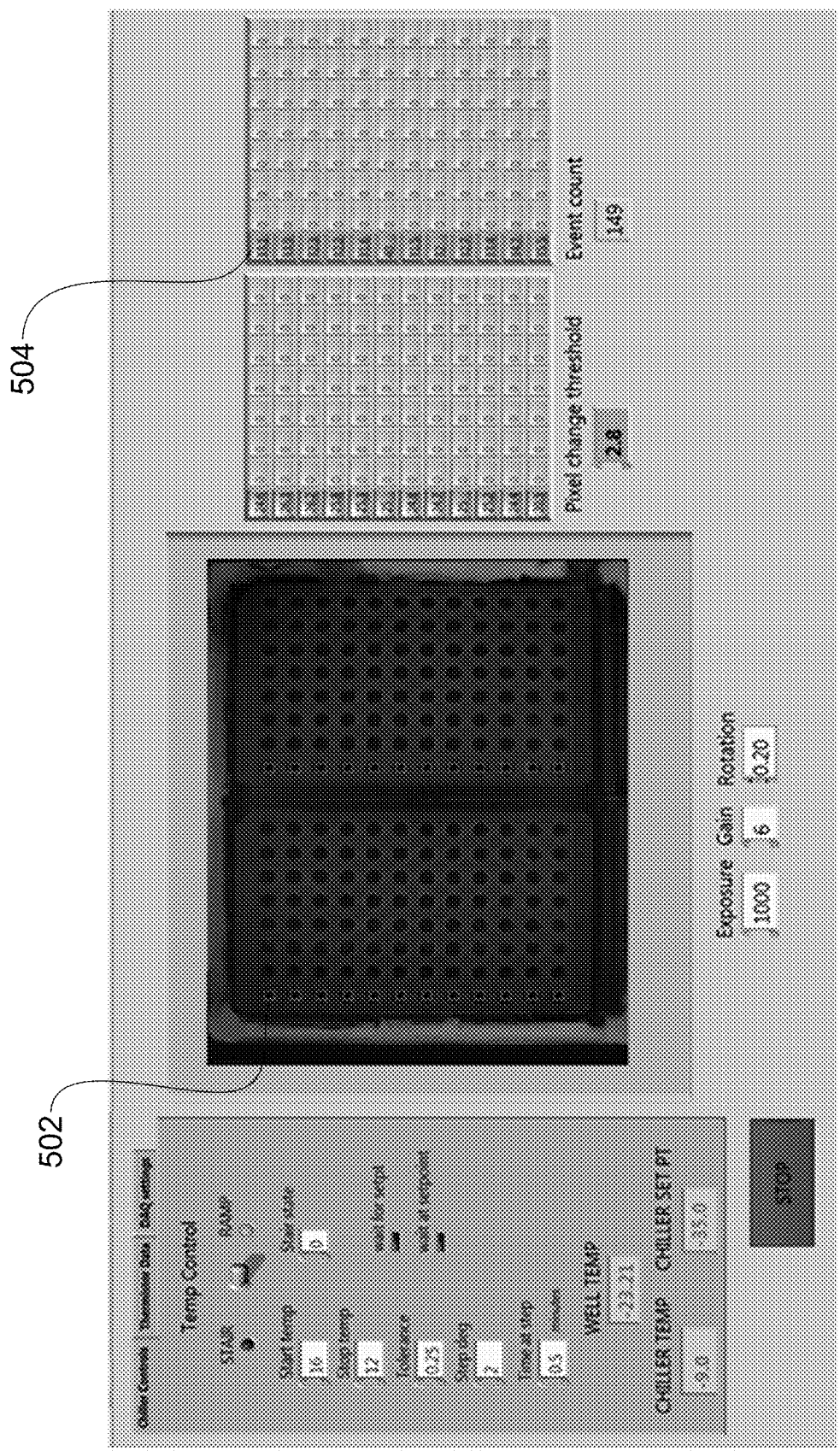
FIG. 5 shows an exemplary screenshot of an interface with chiller controls and well temperature readings on the left, and video stream of image of wells in the middle.

As depicted in FIGS. 4A-4B, the exemplary camera can be controlled with exemplary software, for example, National Instruments Lab-VIEW, which allows the user to adjust imaging parameters such as brightness, exposure, gain, pixel change threshold η and rotation via a graphical user interface control panel shown in FIG. 5. In some embodiments, the exemplary software can be operated from a computing device. The computing device may be a computer or server that includes least one processor and a memory having instructions stored thereupon. The instructions upon execution by the processor configure the computing device to perform the operations disclosed in FIGS. 4 and 5.

Returning to FIG. 4A, the imaging operations (402)-(408) are performed by monitoring the intensity of light reflected from one or more wells. At the scanning operation (402), the computing device uses the camera to scan each well that include sample volumes. As mentioned above, in some embodiments, an exemplary 15×15 pixel box corresponds to an individual sample well. In some embodiments, the computing device checks each camera pixel two times per second. During the scanning operation (402), the computing device uses the camera to record the mean intensity of light, I, reflected from one or more wells, such as from well location (0,0) as shown as an example in FIG. 4C. The mean intensity can be the arithmetic mean of all the pixels in the exemplary 15×15 pixel associated with each well. When droplets freeze, the intensity of the light reflected back to the camera decreases due to the dark background of the inner well block. Returning to FIG. 4A, at the threshold determining operation (404), the computing device determines for a well located at (0,0) (shown as an example in FIG. 4C) and at each new time step ti, whether the difference between the mean intensity I of the well at ti and the mean intensity of the well at the previous time step (ti–I) is greater than a predetermined pixel change threshold η such that |I(ti)–I(ti–I)|>η. In some embodiments, ti refers to a time increment that can be increased by one increment as the process in FIG. 4A is carried out. For example, ti can be increased by one after the moving operation (408). In an exemplary embodiment, at the scanning operation (402), the computing device can scan all pixels for all the wells at two different times and then perform the calculations described above for all the wells. In some embodiments, the i value is the time increment that may run at 2 Hz as a general clock. A benefit of using a 2 Hz clock is that it allows for a convenient scan rate for the camera system.

If the computing device determines that the absolute value of (I (ti)–I (ti–I)) is greater than η for a well, then a freezing event or ice nucleating event is detected for that well and the process moves to the recording operation (406) where a time, freezing temperature, and location of the well are recorded. In some embodiments, the time can be recorded by the computing device based on a local time, or a Greenwich Mean Time (GMT), or a Coordinated Universal Time (UTC). The freezing temperature is measured using the thermistor. In some embodiments, as shown in FIG. 5, the detected freezing events can be highlighted (502) in an image of the sample tray, and displayed in the well matrix diagram on the right with the corresponding highlight (504).

Returning to FIG. 4A, after the recording operation (406), the process moves to the moving operation (408) where the computing devices moves to the next grid box, such as well location (0,1) (shown as an example in FIG. 4C), to perform operations (402)-(406). If the computing device determines that the absolute value of (I (ti)–I (ti–I)) is not greater than η for that well, then the process moves to the moving operation (408).

In some embodiments, prior to performing operation (402), the exposure, gain, pixel change threshold η can be adjusted or specified in a control panel as shown in FIG. 5. By adjusting the exposure, gain, and pixel change threshold the signal-to-noise ratio can be increased by emphasizing the decrease in mean intensity due to freezing and by minimizing the background variation in mean intensity due any oscillation of the chiller unit when the coolant circulator is running. In some embodiments, temperature measurements are made with a thermistor imbedded in the metal block at the base of the sample tray after threading the sensor leads through a small hole drilled in the metal block. In some embodiments, the process of FIG. 4A can be performed during the process of adjusting the temperature of the chiller unit as is described in FIG. 4B below. In some embodiments, the process of FIG. 4A can be performed after the temperature of the chiller unit has been adjusted.

The exemplary flowchart shown in FIG. 4B is used to control the chiller or the refrigerated bath circulator. For instance, the computing device can perform an initialize chiller operation (450) to ramp the temperature of the coolant from room temperature to the input target temperature at a particular rate or to "stair-step" the coolant bath temperature at adjustable, incremented time and temperature steps. As shown in FIG. 5, the option to ramp the temperature or to "stair-step" the temperature can be provided at the initializing chiller operation (450). Further, a variable, such as i, can be set at zero at operation (450). For both the ramp and "stair-step" options, the tolerance e of the chiller or the refrigerated bath circulator thermostat, and ending temperature $T_F$ can be additional input options. Further, for "stair step" option, the starting temperature $T_o$, temperature degree interval, d, and time interval, t can be specified.

At operation (452), the computing device determines whether to adjust the temperature of the chiller based on ramp or "stair-step" settings. If the ramp is selected, the computing device performs the operations on the left side of the branch, and if "stair-step" is selected, the computing device performs the operations on the right side of the branch. Each branch is separately discussed below.

If a ramp is selected, at the setting operation (454), the computing device sets the chiller temperature T to desired end temperature $T_F$. By setting the chiller temperature to $T_F$, the chiller is instructed to ramp (e.g., increase or decrease) the current chiller temperature to the desired end temperature $T_F$. At the reading operation (456), the computing device reads the current chiller temperature using an internal temperature probe located in the coolant of the chiller. In some embodiments, the computing device reads the temperature of the chiller using the chiller's RS-232 serial port. At the first decision operation (458), the computing device determines whether the current temperature is greater than $T_F$. If the current temperature of the chiller is greater than $T_F$, then the chiller is allowed to continue to ramp its temperature to the desired end temperature $T_F$. If the current temperature of the chiller is not greater than $T_F$, then at second decision operation (460), the computing device determines whether the current temperature is equal to $T_F$±a predetermined tolerance value e. Thus, a determination is made whether the current temperature is equal to $T_F$ within a tolerance value. If current temperature is equal to $T_F \pm a$ predetermined tolerance value e, then a holding operation (462) is performed where the computing device waits for a certain amount of time before going back to operation (456). Next, the computing device returns to the reading operation (456) to read the current chiller temperature as previously discussed.

In some embodiments, the order of the two decision operations (458), (460) can be reversed so that the computing device can first determine whether the current temperature is equal to $T_F \pm a$ predetermined tolerance value e and then determine whether the current temperature is greater than $T_F$ if current temperature is not equal to $T_F \pm a$ predetermined tolerance value e.

If a "stair-step" is selected, at the setting operation (464), the computing device sets the chiller temperature T to $(T_0 - i \times d)$, where $T_0$ is the start temperature, i is a variable initialized at operation (450), and d is a predetermined temperature degree interval. By setting the chiller temperature to $(T_0 - i \times d)$, the chiller is instructed to adjust the current temperature of the chiller using d temperature steps. At the reading operation (466), the computing device reads the current chiller temperature.

At the first decision operation (468), the computing device determines whether the current temperature is greater than T. If the current temperature of the chiller is greater than T, then the computing device can wait a predetermined amount of time, for example, 1 second, and then performs the reading operation (466) again. If the current temperature of the chiller is not greater than T, then at second decision operation (470), the computing device determines whether the current temperature is equal to $T \pm a$ predetermined tolerance value e. If current temperature is equal to $T \pm a$ predetermined tolerance value e, then a waiting operation (472) is performed where the process waits for a predetermined time interval, t. In some embodiments, the time interval, t, can be set at the initializing chiller operation. As an example, as shown in FIG. 5, the time interval t is set at 0.5 minutes. At the incrementing operation (474), the computing device increments the value of the variable i by a constant, such a 1, and returns to the setting operation (464) to sets the chiller temperature T as discussed above. Similar to the previous discussion, in some embodiments, the order of the two decision operations (468), (470) can be reversed.

Simulation of Heat Transfer for Immersion Mode Ice Spectroscopy

Model Design

To accurately measure the freezing temperature of INPs in immersion mode spectroscopy, the temperature of each well must be quantified, and the temperature of the sample throughout the volume itself must be homogenous (unstratified). Placing thermistors directly in the sample volume would be ineffective for several reasons, including that (1) the probe itself disrupts the structure of the surface of the droplet and could provide a surface for nucleation, (2) heat conducts through the probe into the sample volume, and (3) probes can introduce contamination. Also, if a probe is placed in a sacrificial sample well, once the well freezes, latent heat is released, and because the thermal properties of ice are different from those of water, the temperature of the frozen well may not be representative of the supercooled liquid wells. Thus, the probe must be placed outside the well volume but in a region of the well block that is thermally homogenous with the sample. Alternatively, if the heat transfer characteristics of the system are resolved, the thermal probe could be placed anywhere in the well block where the offset in temperature between the probe's location and the sample well volume is quantified. The sample volume itself must be thermally homogenous because, if the sample volumes were stratified, a freezing event could be triggered in any of the stratified well layers depending on its temperature and the buoyancy of the ice nucleating entity.

Figure 6D:
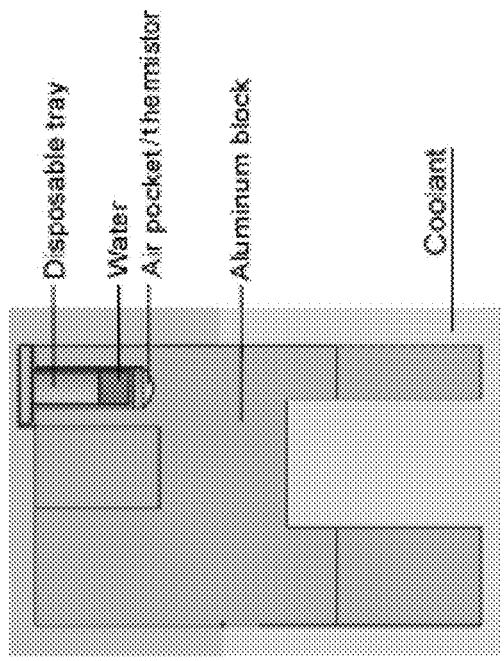
FIGS. 6A-6D shows an exemplary schematic of cut in well block made for heat transfer simulation and mesh applied.
Figure 6B:
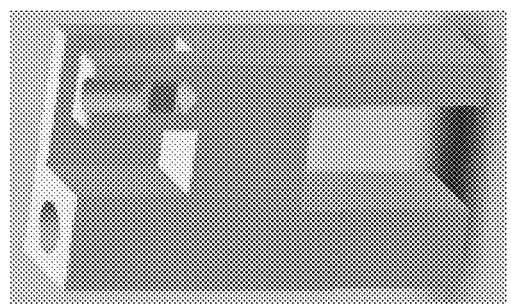
Figure 6A:
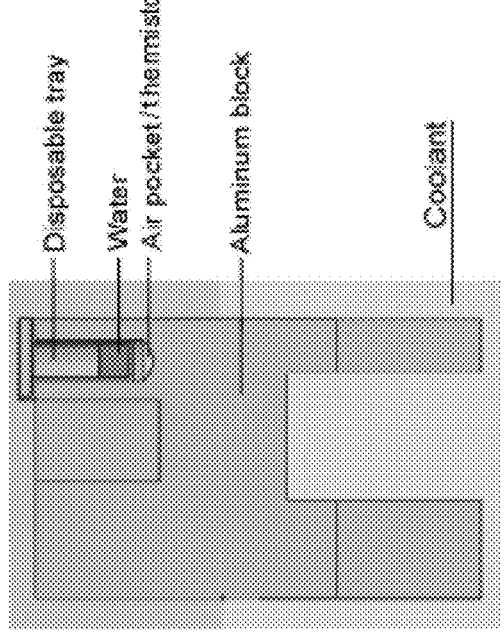
Figure 6C:
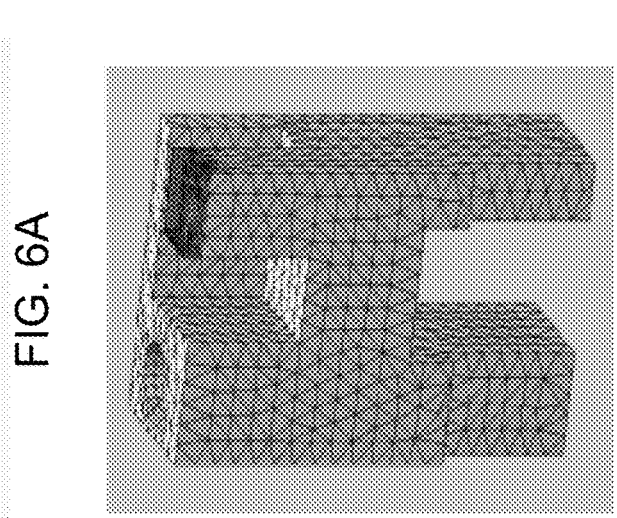

To address the thermal properties of the aluminum block and well-plate system, a finite-element-analysis-based heat transfer simulation was developed using the 3-D design software SOLIDWORKS to investigate the homogeneity of temperature within the 50 µL sample volumes throughout the cooling process and to determine the optimal placement and number of thermistors needed to resolve the temperature of each well. As shown in FIG. 6A, a 3-D model of the aluminum well blocks was designed using the dimensions and material properties of the actual instrument components. As shown in FIG. 6C, in finite-element-analysis heat transfer simulations, a mesh is applied to the modeled object such that, with a given initial temperature and/or heat source at the boundaries, rates of heat transfer and temperature are computed iteratively until solutions converge on the user-defined mesh. Meshing becomes more computationally expensive over curved or complex surfaces, and because the exemplary ice spectrometer's well blocks contain a plurality of wells (e.g., 192 wells) each with a curved inner surface, a cut of the upper left quadrant shown in FIG. 6A was made in the 3-D model to reduce computation time.

Figure 7:
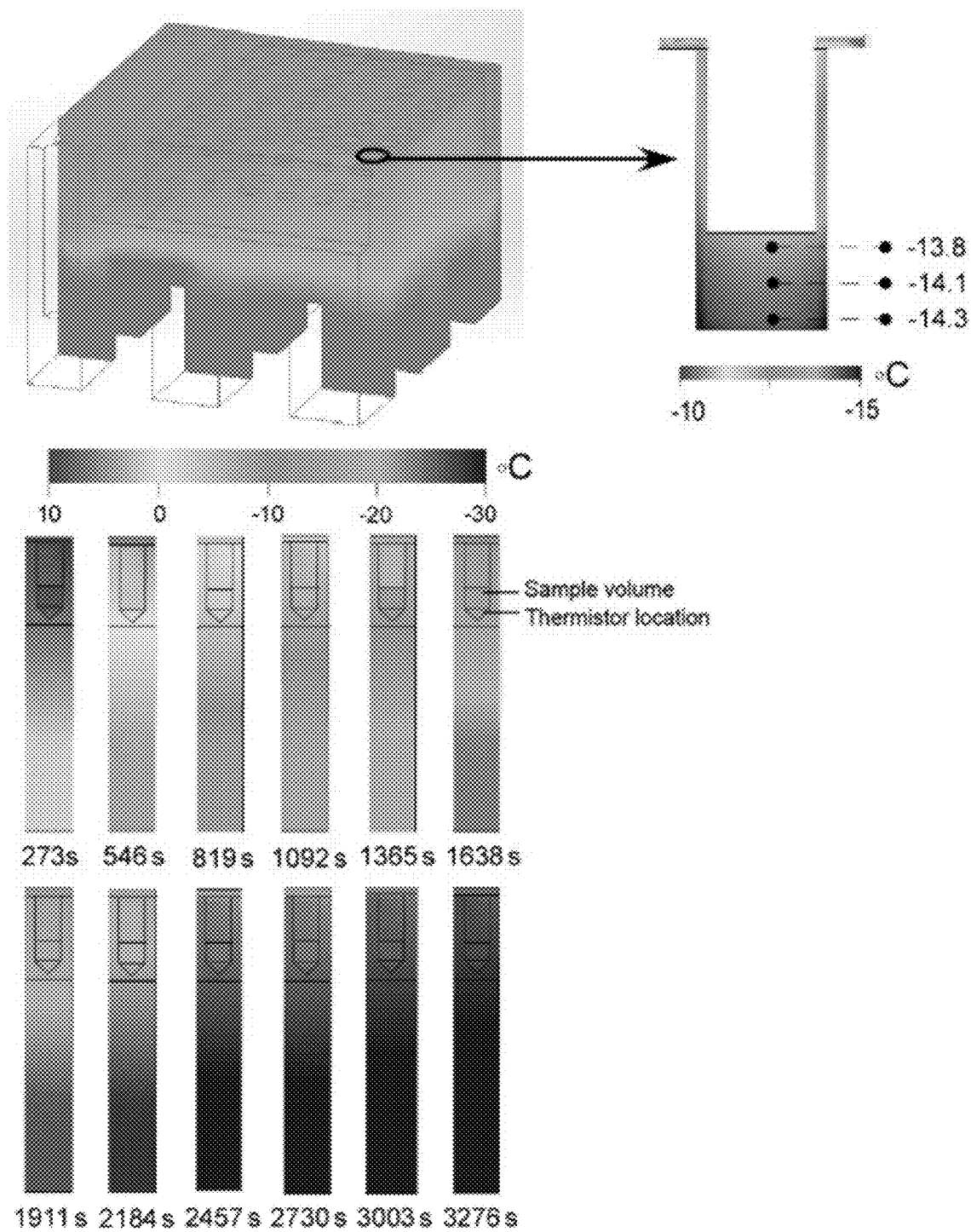
FIG. 7 shows a graphical time series of the heat transfer simulation.
Figure 8:
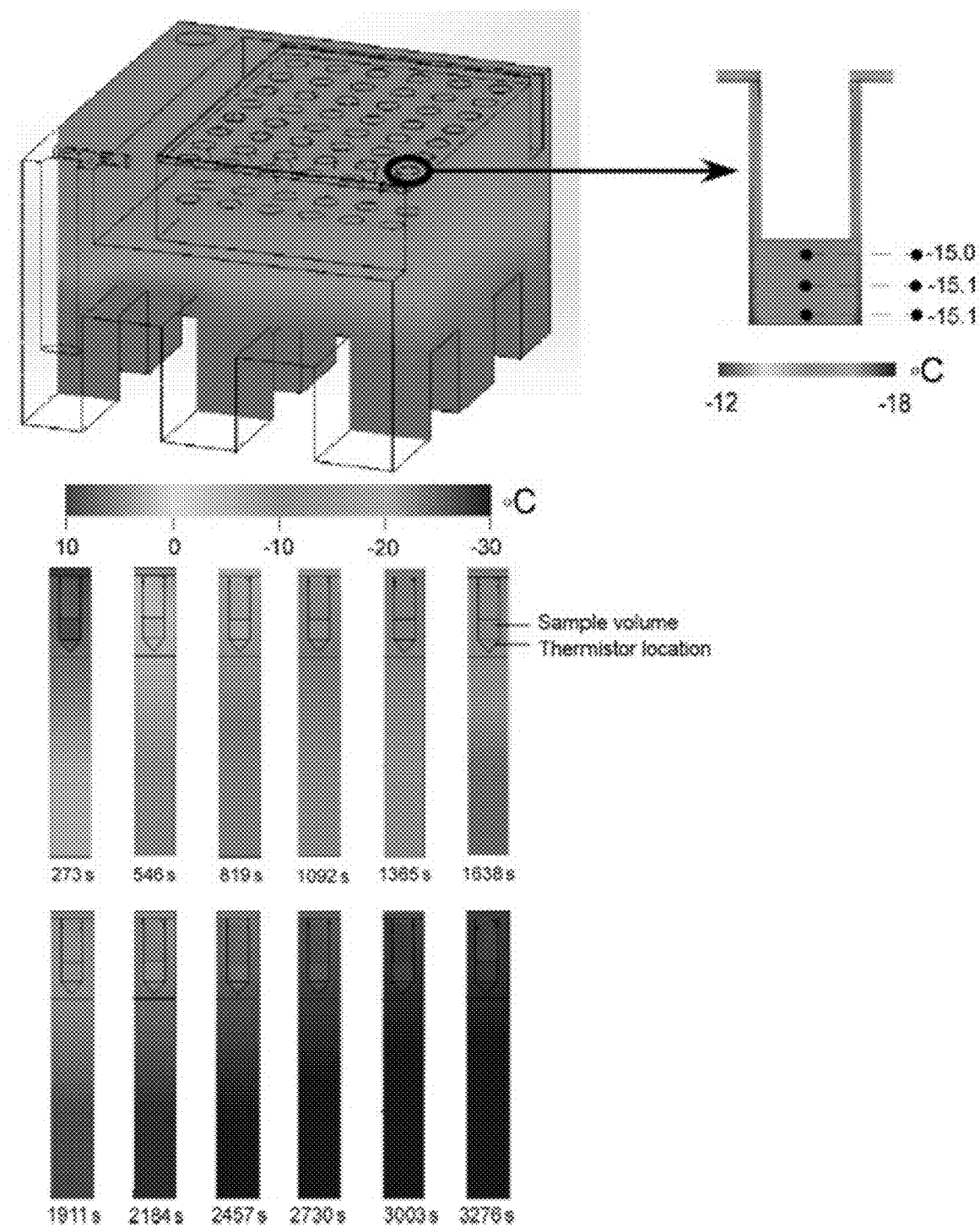
FIG. 8 shows a graphical time series of the heat transfer simulation showing the effects of increasing thermal homogeneity in the cooling environment by efficiently cooling headspace gas on performance of the well block.

In FIG. 6A, the exemplary two metal 96-well blocks ((600a),(600b)) are shown with an exemplary PVC splash guard (602), and the dashed line (604) in the upper-left corner represents the modeled simplifying cut in the well block as further analyzed in FIGS. 7-8. FIGS. 6B and 6D show a close-up of the well block quadrant ((606) in FIG. 6A) featured in the model, including the exemplary metal well block, the exemplary polypropylene sample tray, and a 50 µL sample of water. In some embodiments, the one or more metal blocks include cutouts in the base of the blocks to optimize the thermal inertia and conduction qualities of the one or more blocks. The cutouts allow more coolant or block surface area and faster heat transfer. A pocket of gas between the sample tray and the well block is also modeled due to the slightly imperfect fit of the tray to the well block in the actual instrument. The simplifying modeling cut was justified by making measurements of the horizontal distribution of temperature through the two boundaries of the well region: the nitrogen gas above the well region and the coolant bath, which by design maintains a homogenous temperature throughout the coolant volume. The homogeneity of temperature in the coolant bath was verified using a calibrated thermometer (e.g., Checktemp Pocket Thermometer, Hanna Instruments, accuracy±0.3° C. from −20 to 90° C.). To investigate the horizontal distribution of the temperature of gas across the surface of the well block, in this simulation, four thermistors were placed in the 5 cm headspace between the well block surface and the transparent lid, such as the Plexiglas lid, during repeated cooling processes, and the thermistor temperature was monitored while systematically moving the thermistors through the headspace. The temperature of the nitrogen gas in the headspace was found to be homogenous across the plate within ±0.3° C. (within the error of the calibrated temperature probe).

The horizontal gradient of temperature is constrained by the homogenous temperature across the bottom surface of the well block and a temperature difference of max±0.3° C. across the top surface. The vertical gradient of temperature through the well block, disposable sample tray, and sample volume is not practically measurable and requires resolution through heat transfer simulations in order to determine where probes should be placed to measure temperature of the wells. The larger hole on the left side of the sample well in FIGS. 6A and 6B is where the thermal probes can be placed in some embodiments.

The mesh used is shown in FIG. 6C and was applied using the SOLIDWORKS standard mesh solver. It is composed of discrete, tetrahedral elements that are connected at the three nodes such that they converge through all components in the modeled system. Generally, an aspect ratio around 1 for each element is ideal; for the mesh applied in the heat transfer simulations, 99.1% of the mesh elements have an aspect ratio of less than 3, and 0.00% of mesh elements have an aspect ratio greater than 10. Four Jacobian points, or nodes at the midpoint of element sides, were applied to each element to align with curvature more effectively with linear elements, and the mesh took 1 min, 56 s to converge.

Setup of the Heat Transfer Simulation

The nitrogen and coolant fluid in thermal contact with the sample volumes and well block, respectively, form the thermal boundaries of the simulation. Thus, to quantify the boundary conditions for the heat transfer simulation, temperature measurements were made of the gas temperature above the sample volumes and the coolant temperature during a ramp cooling process, in which the refrigerated bath circulator ran from room temperature to −33° C. at an average cooling rate of −0.87° C. min$^{-1}$ (see FIG. 3). In addition, a hole was drilled into the metal block so that a thermistor could be placed directly underneath a sample well.

Once the thermistor was placed in the block, the hole was sealed with acrylic caulk to prevent coolant fluid from entering the well region, and heat sink compound was applied to the thermistor so that it was in thermal contact with the metal block and the disposable sample tray.

FIG. 3 shows a graph of well temperature vs. temperature offset measured between the base of the well and the air above the well as measured with a thermistor probe (filled circles). The error bars in the larger plot show the range of temperature offsets corresponding to the ±0.3° C. calibration error of the temperature standard. From room temperature to −33° C. as measured at the base of the well, the average cooling rate is −0.87° C. min$^{-1}$. Inset shows cooling performance of the bath coolant and the temperature within the well and gas above well over 3276 s measured by thermistor probes. The average cooling rate at the base of the well during the time period from 0 to −27° C., however, is −0.69° C. min$^{-1}$ because the cooling rate slows as the refrigerated cooling bath approaches its minimum temperature.

In the inset of FIG. 3, the temperature at three locations within the exemplary ice spectrometer is shown after measurement throughout a "ramp" cooling process from 15 to −33° C.: (1) the coolant in contact with the bottom surface of the well block; (2) the gas above the sample volume in the sample tray, or headspace gas; and (3) directly below the sample well. The measurements of temperature of the gas above the sample volume and coolant over 3276 s of cooling are applied as boundary conditions in the heat transfer simulation. The larger plot in FIG. 3 shows the warm temperature offset of the headspace gas from the measured temperature at the well base, and the inset plot shows temperature changes in time, at the three locations over the ramp cooling cycle. The headspace gas and coolant temperature data are applied as boundary conditions in the simulation. FIG. 3 shows that the air above the well region is a maximum of +4.19° C. warmer than the well base, despite the chilled nitrogen pumped over the well region, because the system is imperfectly insulated from the room temperature environment and because there is a slight warming of the gas before it enters the headspace (as described in the sections above). In some embodiments, an transparent lid, such as an acrylic plate, covers the wells as shown in FIG. 1, but the system is not thermally isolated from the environment.

FIG. 6D shows each of the components considered in the model: the metal well block, the disposable sample tray, the gas pocket in the gap between bottom of the sample tray and the well block, and the 50 μL sample water volume. The coolant and the headspace gas were considered in the model as variable thermal loads to the system rather than included as components. Two types of heat transfer were considered during the model analysis: conductive and convective. In the simulation, all of the components shown in FIG. 6D are considered to be bonded, or treated as if heat transfer by conduction occurs in a continuous manner. Heat transfer by conduction is computed at each element of the mesh by the following equation:

$$Q_{conduction} = kA(T_{hot} - T_{cold}) \quad \text{Eq. (2)}$$

where $Q_{conduction}$ is the rate of heat transfer in watts, k is thermal conductivity of the component, A is the heat transfer area defined by the mesh, and $(T_{hot}-T_{cold})$ is the temperature difference between the two mesh elements considered. Thermal conductivity, k, is determined by the material of the component. Values of k used in the simulation are shown in Table 1.

TABLE 1

Elements and properties used in heat transfer simulation

| Components | Material | $k^a$(W mK$^{-2}$) | $h^b$(W m$^{-2}$ K) |
|---|---|---|---|
| Well block | Aluminum 1160 alloy | 200 | 25 |
| Disposable sample tray | Polypropylene | 0.117 | 25 |
| Gas pocket | Air | 0.027 | n/a |
| Liquid INP sample | Water | 0.5 | 191 |

$^a$Davis (1998).
$^b$Yousef et al. (1982). See Sect. 3.2 for calculation of h for liquid sample.
Note:
both k and h are temperature dependent but were used as constants in the simulation due to the insensitivity of the simulation between 0 and −30° C.
n/a = not applicable At all interfaces where the model is in contact with headspace gas, heat transfer by convection is considered. For heat transfer by convection, Eq. (3) is applied at each element:

$$Q_{convection} = hA(T_s - T_f) \quad \text{Eq. (3)}$$

where $Q_{convection}$ is the rate of heat transfer from a body to a fluid in watts, h is the heat transfer coefficient in Wm$^{-2}$ K, and (Ts−Tf) is the difference in temperature between the surface of the body and the fluid. A is the same as above in Eq. (2). The convection of both the gas and the water in the model was considered natural convection rather than forced. Typical ranges for the heat transfer coefficient h for natural convection of air are 5-25 Wm$^{-2}$ K. The model output was insensitive to this range of coefficient variability, and a value of 25 Wm$^{-2}$ K was used. The range of h for natural convection of water, however, is much larger: 2-3000 Wm$^{-2}$ K, so h was estimated by approximating the wells as two vertical plates; calculating the Nusselt number N; and using h=Nk/H, where H is the height of the plates. N was calculated using Eq. (4) for laminar flow:

$$N = 0.68 + \frac{(0.670 Ra^{1/4})}{\left(1 + \left(\frac{0.492}{Pr}\right)^{9/16}\right)^{4/9}} \qquad \text{Eq. (4)}$$

Ra and Pr are the Rayleigh and Prandtl number, respectively, where $$Ra = \frac{g\beta(T - T_\infty)D^3}{\upsilon^2} \cdot Pr \qquad \text{Eq. (5)}$$

And $Pr = \upsilon/\alpha$. $\beta$ is the coefficient of thermal expansion, g is the acceleration due to gravity, T is the temperature of the water volume, $T_\infty$ is the temperature of the air at the surface of the water volume, D is the diameter of the well as measured at the top of the well of the disposable sample tray, $\upsilon$ is dynamic viscosity, and $\alpha$ is the thermal diffusivity. Since $\beta$, $\upsilon$, $\alpha$, and k are temperature-dependent properties, and h is of interest over the supercooled range from 0 to $-25°$ C., N and h were calculated at $-5$, $-15$, and $-25°$ C., using corresponding values of $\beta$, $\upsilon$, $\alpha$, and k, which are shown in Table 2. Thus, h was estimated to be 161, 191, and 202 $Wm^{-2}$ K at $-5$, $-15$, and $-25°$ C., respectively. Within the range 161-202 $Wm^{-2}$ K, the model was insensitive, and a constant value of 191 Wm-2 K was used throughout the simulations.

TABLE 2

Constants used in calculation of heat transfer coefficient h for water in natural convection from $-5$ to $-30°$ C.

| Water temperature T (° C.) | Gas temperature $T_\infty$ (° C.) | $\beta^a$ $(K^{-1}) \times 10^{-6}$ | $\upsilon^b$ $(m^2 s^{-1}) \times 10^{-6}$ | $\alpha^c$ $(m^2 s^{-1}) \times 10^{-7}$ | $k^d$ $(W\ mK^{-1})$ | h $(W\ m^{-2}\ K)$ |
|---|---|---|---|---|---|---|
| $-5.0$ | $-1.6$ | $-168.6$ | 2.0026 | 1.30 | 0.520 | 160.8 |
| $-15.0$ | $-10.3$ | $-450.3$ | 3.0707 | 1.20 | 0.500 | 191.0 |
| $-30.0$ | $-23.4$ | $-1400.0$ | 7.9703 | 1.05 | 0.450 | 201.6 |

[a]Kell (1975).
[b]Dehaoui (2015).
[c]Benchikh (1985).
[d]Biddle (2015).

The simulation was run over 3276 s with two different sets of boundary conditions representing the coolant fluid and headspace gas temperatures. In the first simulation, the coolant fluid temperatures from FIG. 3 were applied, but the difference between the temperature of the headspace gas and that of the well base was multiplied by 2 in order to approximate inefficient cooling of headspace gas. In the second simulation, the gas and coolant temperatures were applied directly from the coolant fluid and headspace gas temperature in FIG. 3. The first condition has warmer headspace gas temperatures than those that were measured during the cooling process on the actual instrument in FIG. 3.

Results—Simulation Results

The results of the heat transfer simulation for the warmer headspace gas condition and the measured gas and coolant temperature conditions are shown in FIGS. 7 and 8. FIG. 7 shows a graphical time series of the heat transfer simulation with the doubling of the offset between the well base and the warmer gas above the well region. The heat distribution is shown in 12 time steps at 273 s intervals over a 3276 s simulation, with the coolant fluid cooling from 15 to $-33°$ C. over that period (i.e., $-0.87°$ C. $\min^{-1}$). Top shows isometric view of the well block (top left quarter) at t=1638 s. Top right shows detailed plane view of well at t=1638 s. Dashed lines indicate temperature of water in the well at three points. Colors indicate temperature referenced by the scale below. Twelve time steps at 273 s intervals show temperature distribution within the well block shown below. The average cooling rate over this time period is $-0.87°$ C. $\min^{-1}$. Results show the stratification of temperature in the sample volume due to warmer air above the well region.

Figure 11:
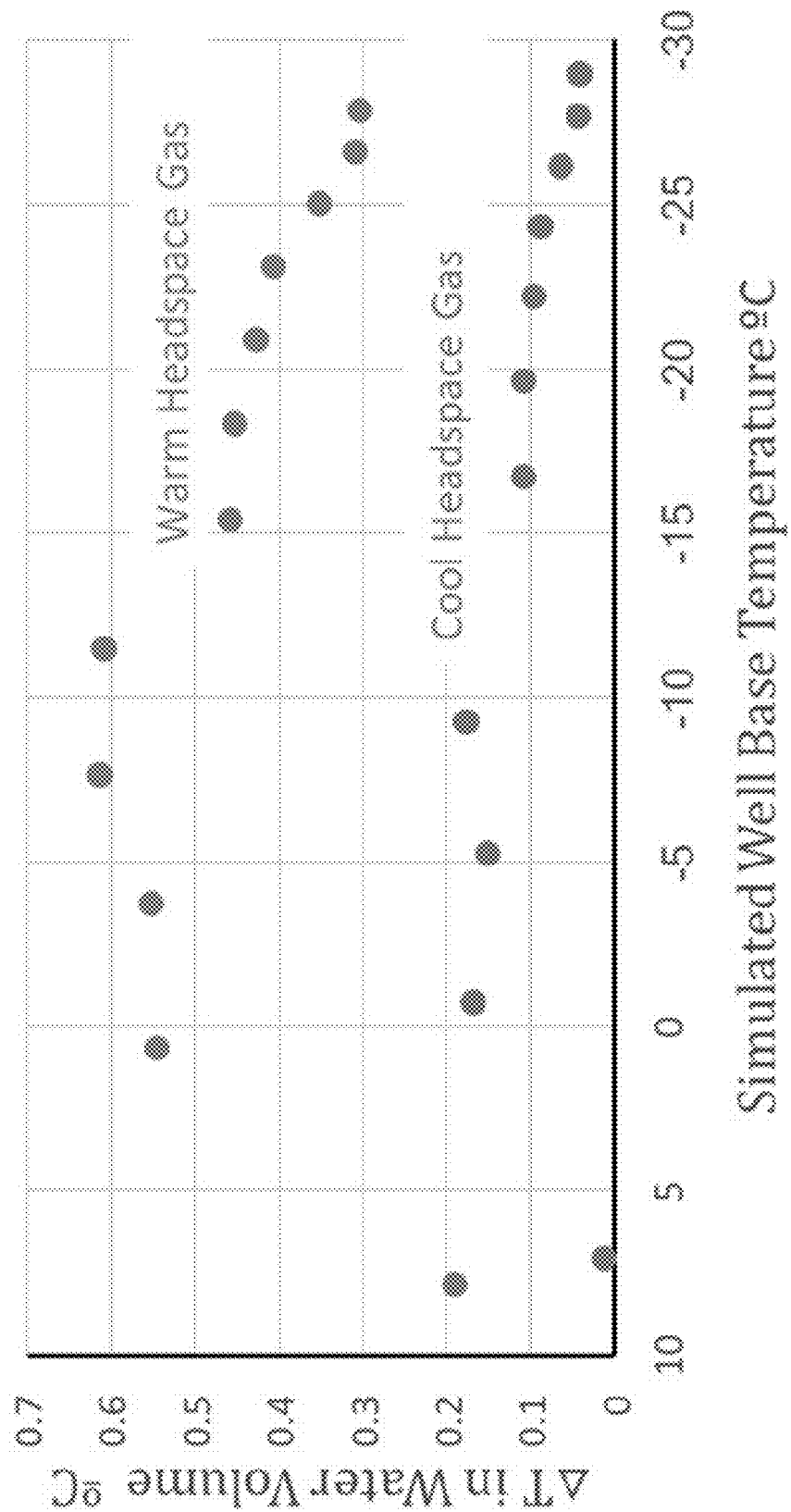
FIG. 11 shows a simulated temperature stratification within the sample volume.

At the top of FIG. 7, an isometric view of the well block at 1638 s is shown, and to the right is a detailed view of the well. The results show the stratification of temperature in the sample volume itself, ranging from $-13.8°$ C. at the skin of the sample volume to $-14.3°$ C. at the bottom of the sample volume. These results demonstrate that the temperature difference of $+6°$ C. between the well and the headspace gas is too large to maintain homogenous temperature within the liquid sample volume, which then becomes stratified by $0.5°$ C. The degree of stratification through the duration of the simulation is shown in FIG. 11, reaching a maximum of $0.6°$ C. In FIG. 11, the difference in simulated temperature between the top and bottom of the 50 µL sample volume is shown for the two simulations. Stratification of the sample volume under normal conditions as measured in the AIS reaches a maximum of $0.2°$ C. Under the warmer headspace gas conditions, stratification increases to a maximum of $0.6°$ C.

FIG. 8 shows a graphical time series of the heat transfer simulation with the measured exemplary ice spectrometer headspace gas temperature and coolant bath temperature conditions from FIG. 3. With an offset between the base of the well and the headspace gas temperature of $+3.0°$ C., stratification has significantly decreased to $0.1°$ C. from top to bottom of the sample volume, which is within the error of the thermal probe or thermistor (see FIG. 11). As in FIG. 7, the top shows isometric view of the well block at t=1638 s. Dashed lines indicate temperature of water in the well at three points. Colors indicate temperature referenced by the scale below. Twelve time steps at 273 s intervals showing temperature distribution within the well block shown below. The average cooling rate over this time period is $-0.87$ C $\min^{-1}$. Results show the decreased stratification of temperature in the well due to cooler air above the well region (air temperature offset varied approximately $+2$-$4°$ C. from the bath coolant temperature as shown in FIG. 3).

The results also show that the distribution of heat throughout the well block requires careful placement of the temperature probe such that the temperature of the probe location is accurately indicating the temperature of the sample volume. In each of the simulations, the sample water volume comprises the warmest body in the model assembly. Throughout the modeled assembly, the temperature in the gas pocket underneath the well of the polypropylene disposable tray was the region closest in temperature to the sample volume, albeit still colder by as much as −1.8° C. Due to strong temperature gradients between the water sample and the immediately surrounding aluminum block, small variations in probe location can result in disproportionately large temperature offsets from the sample volume. At 1638 s in the second simulation, which applies the gas and coolant temperature conditions as measured on the exemplary ice spectrometer (FIG. 3), the temperature decreases 1.8° C. from base of the well of the polypropylene disposable tray through the gas pocket to the aluminum surface of the well block over a distance of 2.5 mm, resulting in an offset of −1.6° C. between the average temperature of the air pocket and that of the sample volume. This could be caused by the high specific heat of the water volume relative to the aluminum, and the insulating thermal properties of the polypropylene tray could be responsible for the strong temperature gradient. In the exemplary ice spectrometer, the thermal probe or thermistor can be located in this gas pocket, and the simulation results suggest that at this location there could be up to a −1.8° C. cold bias in the INP freezing temperature measurements. Thus, during ramping of the coolant bath from room temperature to −33° C. at about −0.87° C. $\min^{-1}$, there is nowhere to place a probe in the aluminum block where the temperature perfectly matches that of the liquid sample volume (within ≪1° C.). The offset in temperature between the probe and the sample temperature was quantified so that recorded temperatures can be adjusted accordingly.

In order to verify the simulation output so that offsets found can be applied quantitatively to freezing temperature measurements, simulated temperatures were checked against measurements that were independent of the simulation. Since the entire surface of the system was constrained by boundary conditions in the simulation, the measurements from inside of the well block at the well base (shown in FIG. 3) were used for comparison with the simulation output at the same location. Results of the comparison over the 12 time steps of the simulation are shown in FIG. 10.

Figure 10:
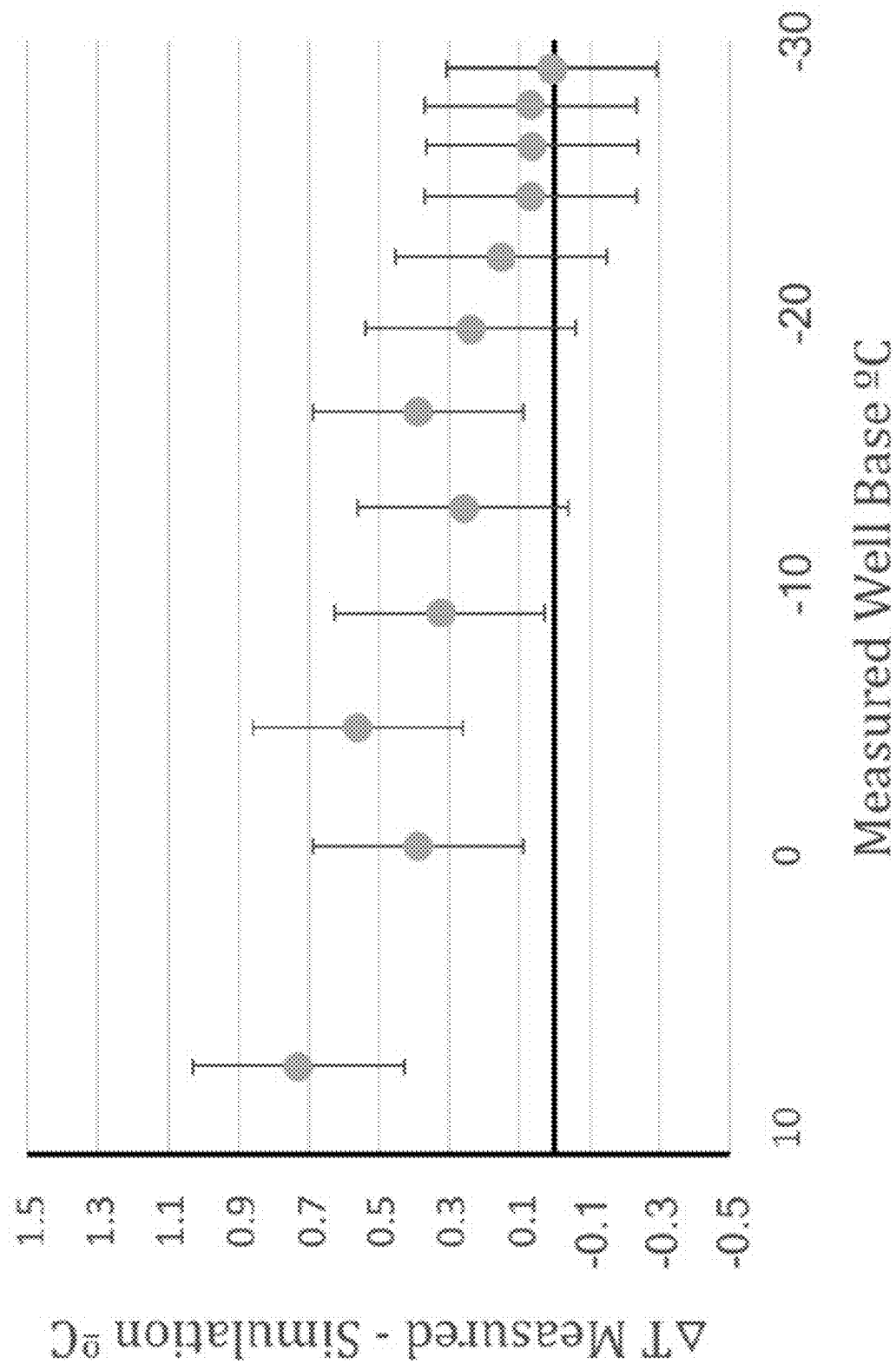
FIG. 10 shows a difference between measured and simulated temperature of the air pocket in the well base.
Figure 12:
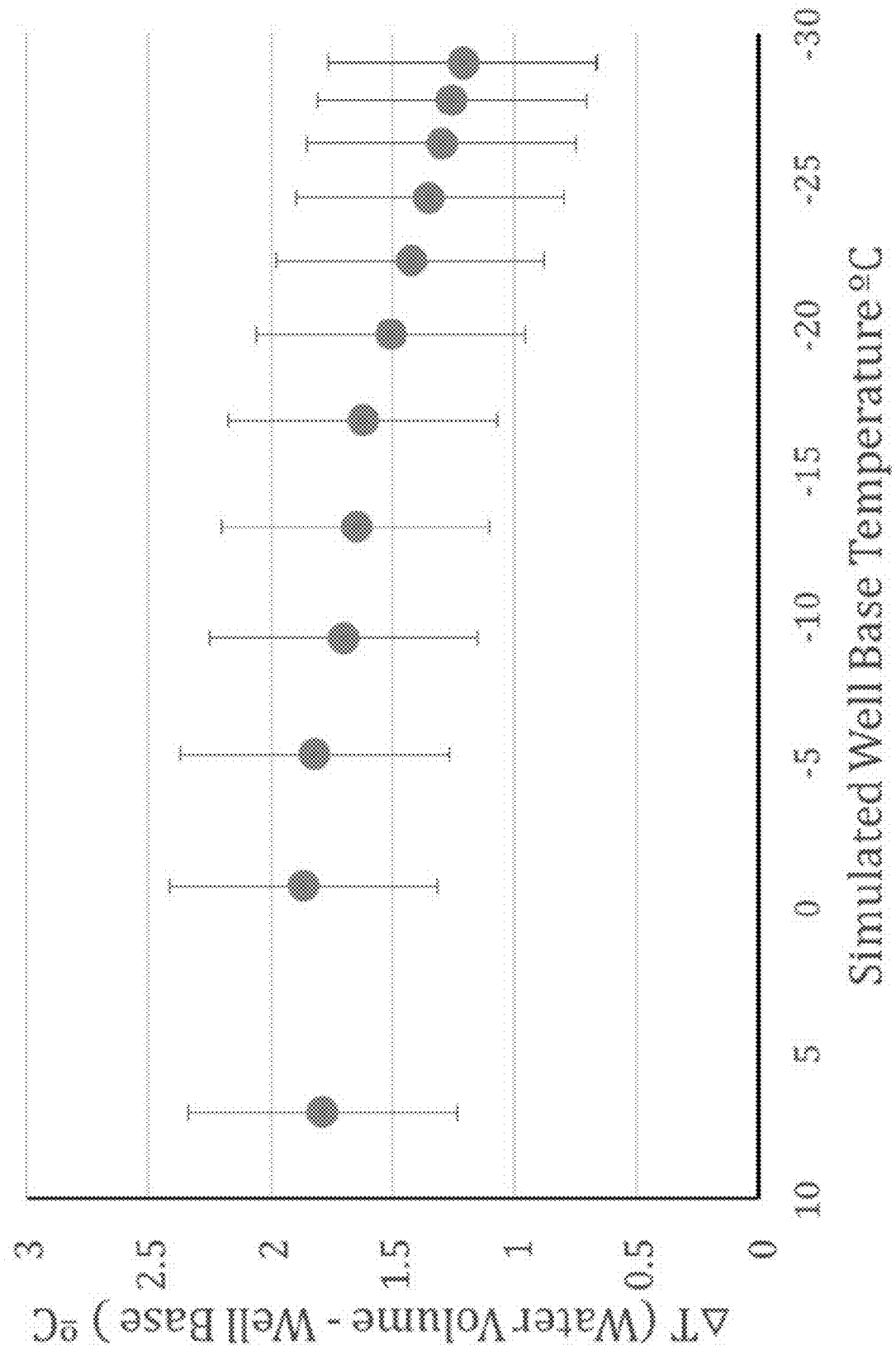
FIG. 12 shows a simulated temperature offset between the sample volume and the well base.
Figure 13:
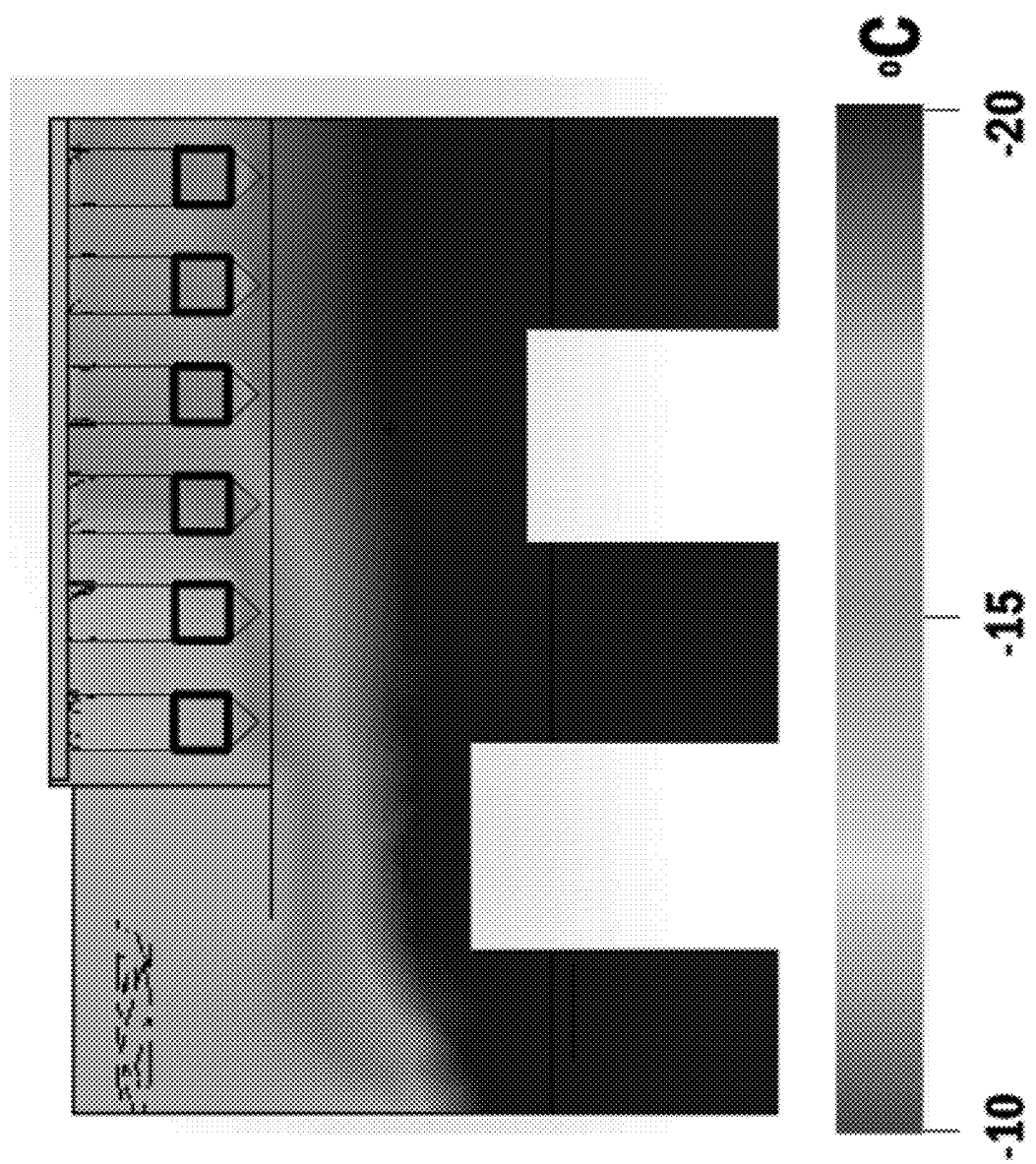
FIG. 13 shows a spatial temperature gradient in sample volume temperature.

In FIG. 10, the maximum difference between the predicted temperature and the measured temperature over the twelve time steps of the 3276 s simulation was 0.6° C. at subzero temperatures. The error bars shown represent the uncertainty of the thermal probe at the well base, ±0.3° C. At subzero temperatures, the maximum difference between the measured and simulated temperatures was 0.6° C. at t=819 s, decreasing to values below the error of the thermistor for most of the simulation±0.6° C. is assumed to be the uncertainty of the simulation. The measured temperature was consistently slightly warmer than the simulated temperature, possibly because the hole drilled into the aluminum well block was not modeled. In the second simulation using measured boundary conditions, the average temperature of the sample volume was compared with the average temperature of the air pocket in which the thermistor is placed throughout the 3276 s simulation (see FIG. 12), in order to quantify the offset between the thermistor and the sample. In FIG. 12, the average sample volume temperature is warmer than the air pocket in the well base throughout the 3276 s simulation. Error bars reflect the uncertainty of the simulation based on the difference between measured and simulated temperature of the well base The air pocket temperatures are consistently colder than the sample volume temperatures, ranging from −1.8 to −1.2° C. over the 3276 s simulation. Offsets in temperature between the 192 wells also exist in the exemplary ice spectrometer and are shown in FIG. 13. In FIG. 13, a cross-section of top left quadrant of the well block is shown at 1638 s. The sample volumes are outlined by the thick black rectangles. The leftmost sample volumes are closer to the outer edges of the well block, whereas the rightmost sample volumes are closer to the interior of the block. Thus, the leftmost sample volumes that are closer to the outer edges of the well block are warmer than the sample volumes along the interior of the well block, with a maximum difference of 2.2° C. Sample volumes in wells near the outer perimeter are up to +2.2° C. warmer than sample volumes near the center of the well block. Detailed analyses of the offsets along the x and y axis over the 3276 s simulation are not shown because there is only one thermistor embedded in the well block for the simulation, so verification of the simulation's temperature gradient in x and y was not possible without further modifications to the well block. Additional thermistors embedded within the well block can be used to verify the simulation output so that measurements can be adjusted with offsets due to the gradient in x and y as well as z. However, the maximum offset found between wells in x and y, +2.2°, will be represented as the uncertainty associated with the measurements reported in the following sections.

Results—Performance of the Exemplary Ice Spectrometer: Comparison with Six Other Immersion Mode Ice Nucleation Measurement Techniques The accuracy of the exemplary ice spectrometer INP concentration measurements were evaluated using a standard, well-characterized test dust that has previously been used to compare immersion mode ice nucleation measurement techniques, illite NX (Arginotech, NX nanopowder). A suspension of dust and Milli-Q ultrapure water was prepared in a sterile 50 mL centrifuge tube (Corning) using a sample from the same batch of illite NX, a study of 17 immersion mode ice nucleation measurement techniques. Twenty milligrams of illite NX was immersed in 500 mL of ultrapure water, resulting in a $4.0\times10^{-3}$ wt % solution. Two more dilutions were made by immersing 25 mg of illite NX in 50 mL of ultrapure water and diluting again by factors of 1/10 and 1/100, resulting in solutions of $5.0\times10^{-2}$ and $5.0\times10^{-3}$ wt %, respectively. A final solution was prepared by starting with 300 mg in 50 mL of ultrapure water and then diluting by factors of 1/100 and 1/1000, resulting in a solution of $6.0\times10^{-6}$ wt %. For comparison, in Hiranuma et al. (2015), droplet assays were intercompared using illite NX suspensions of varying dilutions within the range of $3.1\times10^{-6}$ wt % to 1.0 wt %. Higher concentrations of illite NX solution were not measured using the exemplary ice spectrometer because the software requires an optically clear solution to detect freezing events. Fifty-microliter aliquots of the suspension were loaded into 24 wells of the disposable sample tray (Life Science Products™ 96-well PCR plates), and 24 adjacent wells were filled with 50 µL aliquots of Milli-Q water. Prior to loading, the exemplary Plexiglas lid was cleaned with an isopropyl-alcohol-based surface cleaner, rinsed three times with Milli-Q, and dried with clean compressed air, and nitrogen was pumped over the well region at 0.25 L $\min^{-1}$ for 20 min to purge the lines of any dust. The loaded and covered sample was then cooled from room temperature to −27° C. (with an average cooling rate of −0.87° C. $\min^{-1}$), at which point the Milli-Q water had frozen in all wells. The experiment was repeated four times. Freezing events were detected using the process described in FIG. 4A, and the time of freezing, well temperature, and sample number were recorded into an ASCII file for further analysis.

Cumulative concentration of INPs per volume per 0.25° C. were calculated using Eq. (1). In order to compare directly with Hiranuma et al. (2015), cumulative concentrations of INPs were converted into a surface site density, ns,BET. The specifics of the parameterization are in Hiranuma et al. (2014), but briefly, the parameterizations are based on BET (Brunauer-Emmet-Teller) N2-adsorption-based specific surface area (SSA) in which the particle surface area is measured based on the quantities of a variety of gases that form monolayers on the surface of the particle. The SSA of the illite NX sample used in Hiranuma et al. (2015) was 124 $m^2 g^{-1}$, and the mass concentration (m) of the four illite NX solutions processed in the exemplary ice spectrometer ranged from $6.0 \times 10^{-6}$ to $5.0 \times 10^{-2}$ g $mL^{-1}$. The exemplary ice spectrometer measurement results in terms of cumulative INPs per volume were converted to the surface site density, $n_{s,BET}$, using the mass concentration and specific site density as follows:

$$n_{s,BET} = \frac{\left(\frac{INPs}{mL}\right)}{SSA \cdot m} \quad \text{Eq. (6)}$$

Figure 9:
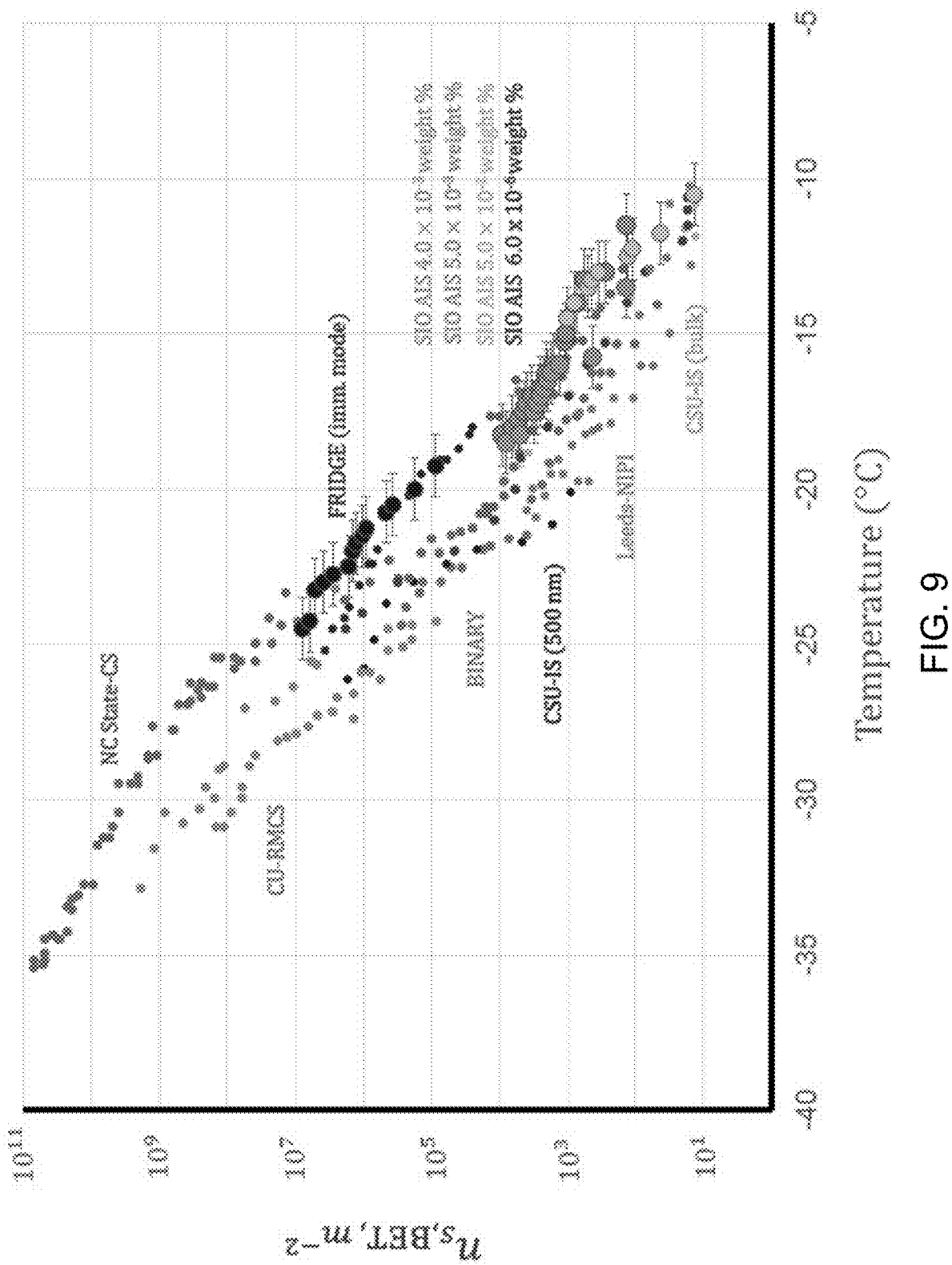
FIG. 9 shows an immersion freezing spectra of illite NX particles in terms of $n_{s,BET}$ (T) for comparison of SIO AIS against six other immersion mode techniques reported.

In FIG. 9, the measured illite NX spectra are shown with 6 of the 17 total ice nucleation measurement techniques from Hiranuma et al. (2015). The six instruments made wet-suspension-based measurements of illite NX in ultra-pure water rather than dry-particle-based measurements and thus should more directly compare to those of the exemplary ice spectrometer. $N_{s,BET}$ is used to estimate ice nucleation surface site density from an N2-adsorption-based specific surface area. CSU-IS (500 nm) represents measurements made on illite NX particles that were mobility-diameter-size-selected, whereas all other measurements reported were of bulk illite NX samples. Four different dilutions of illite NX suspensions were measured by the SIO AIS: $4.0 \times 10^{-3}$ wt %, $5.0 \times 10^{-3}$ wt %, $5.0 \times 10^{-2}$ wt %, and $6.0 \times 10^{-6}$ wt %. SIO AIS measurements fall on the warm side of the spectra.

Temperature offsets between the thermistor and the sample volumes due to the consistently colder location of the thermistor, ±1.8° C., and the warmer wells near the perimeter of the well block, ±2.2° C. (as discussed above), are represented in the error bars on the exemplary ice spectrometer measurements. The ice nucleation surface site density spectra of the six measurements fall within a range of about 5° C., and the exemplary ice spectrometer measurements compare favorably to those of the other six techniques through its final temperature of −25° C. However, the exemplary ice spectrometer measurements fall on the warmer side of the temperature spectrum from −10 to −25° C. Based on the results of the heat transfer simulations discussed in sections above, differences in the cooling process type (stair step or ramp), location of temperature probe or method of freezing temperature measurement could have strong influences on reported freezing temperatures. These factors might account for some of the 8° C. (or 5° C. for wet-suspension droplet assay techniques) spread in spectra reported.

DISCUSSION

The exemplary immersion mode ice spectrometer can fit inside a refrigerated circulating coolant bath and can be controlled using the exemplary process of FIG. 4B.

The heat transfer properties of the exemplary ice spectrometer were characterized using finite-element-analysis heat transfer simulations, with measured temperatures of the well block headspace gas and the coolant bath applied as boundary conditions. Heat transfer by conduction and convection was considered. The results of the simulations showed that efficient cooling of the well block headspace, with a maximum +4° C. offset between the base of the well and the headspace gas or +11° C. between the coolant bath and the headspace gas, is necessary to ensure that the liquid sample volume is unstratified within the error of the thermal probe, ±0.2° C., so that the well-freezing temperature is representative of the population INPs in the well. The results also demonstrate a strong temperature gradient from the sample volume to the polypropylene and aluminum immediately surrounding the sample, of up to −1.8° C. in the 2.5 mm gap. Thus the temperature measurement in the exemplary ice spectrometer is sensitive to the location of the thermal probe. In the simulation, the only region with a temperature consistent with the sample volume was the top of the gas pocket between the bottom of the polypropylene disposable tray and the aluminum block. However, a thermistor probe cannot physically fit in this small region, so INP freezing temperature measurements are likely biased by the thermistors contact with the aluminum block. An offset between the thermistor location and the sample volume was quantified, first by verifying the simulation output using a thermistor embedded in the well block (see FIG. 11), then using the simulation output to determine the offset to apply to the recorded measurements. For other immersion mode droplet assay INP measurement techniques, variation in heat transfer properties and thermal probe placements may result in higher or lower accuracy of INP freezing temperature measurement, but the sensitivity of the temperature gradient within the droplet to the thermal heterogeneity of its cooling environment, as well as that of the temperature measurement to thermal probe placement, motivates careful study of the effect of heat transfer properties of the various techniques. The heat transfer simulations applied here could support investigations of bias in temperature measurement for INP measurement techniques, enable higher accuracy in INP freezing temperature measurements, and ultimately help decrease disparities between various instruments. INP concentrations applied in cloud and climate models must be accurate within an order of 10 to avoid propagation of error leading to significantly different cloud properties, and as measurements typically show INP concentrations increasing with decreasing temperature in complex multi-exponential functions, an 8° C. uncertainty in freezing temperature measurement could result in vast differences in model output. Heat transfer simulations could prove particularly useful in studies of the role of varied cooling rates on assessment of ice nucleation activity in different devices due to the stochastic or time-dependent nature of droplet freezing at a given temperature. In such an investigation, it is important to separate the impact of time dependence of the ice nucleating entity from variations due to temperature gradients between the location of the thermal probe and the sample volume.

Fast cooling of samples (>1° C. min$^{-1}$) has been discussed as a potential source of stratification of temperature between the substrate and the droplets, or within the droplets; conversely, that chilled nitrogen in the headspace might not be necessary to avoid stratification. However, the heat transfer simulation results below show that, even with cooling rates below 1° C. min$^{-1}$, stratification within the sample volume can occur and that the temperature of nitrogen gas in the headspace may play a significant role in controlling temperature stratification within the droplets.

The performance of the exemplary ice spectrometer was evaluated using measurements of illite NX, a well-characterized test dust that has been used to intercompare 17 immersion mode INP measurement techniques. Four different dilutions of illite NX suspension were measured: $4.0\times10^{-3}$, $5.0\times10^{-3}$, $5.0\times10^{-2}$, and $6.0\times10^{-6}$ wt %. These concentrations fall in the middle to the lower end of the range of suspension concentrations ($3.0\times10^{-6}$ to 1.0 wt %) measured by the six selected droplet assay INP measurement techniques in Hiranuma et al. (2015) (see FIG. 9). Measurements of specific site density compare well with the six droplet assay techniques from the intercomparison study (Hiranuma et al., 2015), falling on the warmer side of the 5° C. spread in the reported spectra from −10 to −25° C.

The exemplary ice spectrometer can enable autonomous measurement of INP concentrations, can measure concentrations of INPs with activation temperatures in the range 0 to −25° C., can process up to seven samples per hour using 24 wells per sample (including time for loading samples), and has characterized heat transfer properties so that stratification, temperature offsets from well to well, and offsets between temperature probes and the sample volume can be studied.

The term "exemplary" is used to mean "an example of" and, unless otherwise stated, does not imply an ideal or a preferred embodiment.

Some of the embodiments described herein are described in the general context of methods or processes, which may be implemented in one embodiment by a computer program product, embodied in a computer-readable medium, including computer-executable instructions, such as program code, executed by computers in networked environments. A computer-readable medium may include removable and non-removable storage devices including, but not limited to, Read Only Memory (ROM), Random Access Memory (RAM), compact discs (CDs), digital versatile discs (DVD), etc. Therefore, the computer-readable media can include a non-transitory storage media. Generally, program modules may include routines, programs, objects, components, data structures, etc. that perform particular tasks or implement particular abstract data types. Computer- or processor-executable instructions, associated data structures, and program modules represent examples of program code for executing steps of the methods disclosed herein. The particular sequence of such executable instructions or associated data structures represents examples of corresponding acts for implementing the functions described in such steps or processes.

Some of the disclosed embodiments can be implemented as devices or modules using hardware circuits, software, or combinations thereof. For example, a hardware circuit implementation can include discrete analog and/or digital components that are, for example, integrated as part of a printed circuit board. Alternatively, or additionally, the disclosed components or modules can be implemented as an Application Specific Integrated Circuit (ASIC) and/or as a Field Programmable Gate Array (FPGA) device. Some implementations may additionally or alternatively include a digital signal processor (DSP) that is a specialized microprocessor with an architecture optimized for the operational needs of digital signal processing associated with the disclosed functionalities of this application. Similarly, the various components or sub-components within each module may be implemented in software, hardware or firmware. The connectivity between the modules and/or components within the modules may be provided using any one of the connectivity methods and media that is known in the art, including, but not limited to, communications over the Internet, wired, or wireless networks using the appropriate protocols.

While this document contains many specifics, these should not be construed as limitations on the scope of an invention that is claimed or of what may be claimed, but rather as descriptions of features specific to particular embodiments. Certain features that are described in this document in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this disclosure.

What is claimed are techniques and structures as described and shown, including:

1. A spectrometer, comprising:
    a housing located on top of a chiller unit, the chiller unit comprising:
        a cavity configured to be filled with a coolant, and
        a coil positioned to be submerged in presence of the coolant;
    a hose to supply cold gas from the coil to a well area in the housing, the hose having a first end and the second end, wherein the first end is coupled to one end of the coil and the second end is coupled to a side of the housing;
    one or more metal blocks located inside the cavity of the chiller unit and positioned to be partially immersed in the coolant, wherein each metal block has a top surface with a plurality of indentations;
    a thermistor located in one of the one or more metal blocks to measure temperature of a region surrounding the one or more metal blocks;
    one or more sample trays located on top of the one or more metal blocks, wherein each sample tray comprises a plurality of wells that extend downwards from a bottom of each sample tray and that fit within the plurality of indentations of the one or more metal blocks;
    a lid to cover the plurality of wells to insulate air above the plurality of wells from room temperature air;
    a camera located on a top surface of the housing to capture images of samples located in the plurality of wells;
    a plurality of light sources located on the housing to provide a stable lighting environment in the housing; and a computing device comprising a processor and a memory including instructions stored thereon, wherein the instructions upon execution by the processor configure the computing device to:

program the chiller unit to reach a certain end temperature to freeze samples located in the plurality of wells; and record, using the camera, an intensity of light reflected from the samples located in the plurality of wells at least during the temperature of the chiller unit is adjusted.

2. The spectrometer of claim 1, wherein the chiller unit is programmed by the computing device configured to:

send instruction indicative of an option for temperature control of the chiller unit; and selectively based on the option chose between a ramp function and a stepwise adjustment function.

3. The spectrometer of claim 2, wherein in response to the option being the ramp function, the computing device configured to:

set a temperature of the chiller unit to reach the certain end temperature;

read a current temperature of the chiller unit;

adjust the temperature in response to a determination that the current temperature is greater than the certain end temperature; and wait for a certain amount of time in response to a determination that the current temperature is equal to the certain end temperature within a tolerance value.

4. The spectrometer of claim 2, wherein in response to the option being the stepwise adjustment function, the computing device configured to:

set a temperature of the chiller unit to reach an intermediate temperature value;

read a current temperature of the chiller unit;

adjust the temperature in response to a determination that the current temperature is greater than the intermediate temperature value;

wait a predetermined time interval in response to a determination that the current temperature is equal to the intermediate temperature value within a tolerance value;

increase a predetermined variable; and set the temperature of the chiller unit to reach another intermediate temperature value.

5. The spectrometer of claim 4, wherein the intermediate temperature value is equal to a start temperature minus the predetermined variable multiplied by a temperature interval.

6. The spectrometer of claim 1, wherein the intensity of light is recorded by the computing device configured to:

record, using the camera, a first mean intensity of light reflected from one or more samples in one or more wells at a first time value;

record, using the camera, a second mean intensity of light reflected from the one or more samples in the one or more wells at a second time value, wherein the second time value logically comes after the first time value; and record a time, a freezing temperature measured using the thermistor, and a location of the one or more wells in response to a determination for each sample that an absolute value of a difference between the first mean intensity and the second mean intensity is greater than a predetermined threshold.

7. The spectrometer of claim 1, wherein the coil is a coiled copper tube.

8. The spectrometer of claim 1, further comprising:

a splash guard fitted on the one or more metal blocks to prevent contamination of the plurality of wells by the coolant bath.

9. The spectrometer of claim 1, wherein the one or more metal blocks comprises any one of aluminum, copper, and stainless steel.

10. The spectrometer of claim 1, wherein each of the one or more metal blocks includes a base with a cutout region.

11. The spectrometer of claim 1, wherein the one or more sample trays comprises polypropylene.

12. The spectrometer of claim 1, wherein the plurality of light sources are located on at least two sides of the housing.

13. The spectrometer of claim 1, wherein the lid includes Plexiglas material.

14. The spectrometer of claim 1, wherein the housing is made from white cast acrylic sheet.

15. The spectrometer of claim 1, further comprising an adjustable cradle that holds the camera and allows a camera lens to be aligned over a center region of the one or more metal blocks.

16. The spectrometer of claim 1, wherein the thermistor is imbedded in the one or more metal blocks.

* * * * *